United States Patent [19]

Petersen et al.

[11] Patent Number: 5,679,689
[45] Date of Patent: Oct. 21, 1997

[54] QUINOLONE- AND NAPHTHYRIDONECARBOXYLIC ACID DERIVATIVES

[75] Inventors: Uwe Petersen, Leverkusen; Thomas Schenke, Bergisch Gladbach; Klaus-Dieter Bremm, Recklinghausen; Rainer Endermann, Wuppertal, all of Germany

[73] Assignee: Bayer Aktiengesellschaft, Leverkusen, Germany

[21] Appl. No.: 534,369

[22] Filed: Sep. 27, 1995

[30] Foreign Application Priority Data

Oct. 4, 1994 [DE] Germany .................. 44 35 479.7

[51] Int. Cl.$^6$ .................. A61K 31/47; C07D 215/14
[52] U.S. Cl. .................. 514/312; 514/285; 514/287; 514/291; 514/293; 514/300; 514/301; 514/302; 546/61; 546/65; 546/80; 546/83; 546/89; 546/98; 546/123; 546/156; 546/158
[58] Field of Search .................. 546/156, 157, 546/158, 61, 65, 80, 83, 89, 98, 123; 514/285, 287, 291, 293, 300, 301, 302, 312

[56] References Cited

U.S. PATENT DOCUMENTS 5,508,278  4/1996  Jaetsch et al. .................. 514/229.2

FOREIGN PATENT DOCUMENTS

| 0429304 | 5/1991 | European Pat. Off. . |
| 0 516 861 A1 | 12/1992 | European Pat. Off. . |
| 0520240 | 12/1992 | European Pat. Off. . |
| 0 588 166 A2 | 3/1994 | European Pat. Off. . |
| 4329600 | 3/1995 | Germany . |
| 9521163 | 8/1995 | WIPO . |

OTHER PUBLICATIONS

Derwent Abstract of JP 04-253923 (1990) Week 9243, pp. 9-10.
M. Sato et al, J. Med. Chem., vol. 35, pp. 4745-4750 (1992).
P. Newman, "Optical Resolution Procedures for Chemical Compounds", vol. 1, Optical Resolution Information Center, Manhattan College, Riverdale, N.Y. (1978).
G. Blaschke, Angew. Chem. Int. Ed. Eng., vol. 19, pp. 13-24 (1980).

*Primary Examiner*—C. Warren Ivy
*Assistant Examiner*—Garth M. Dahler

*Attorney, Agent, or Firm*—Sprung Kramer Schaefer & Briscoe

[57] ABSTRACT

Disclosed are new quinolone- and naphthyridonecarboxylic acid derivatives of the formula:

wherein

T represents a radical of the formula:

and the other radicals are as disclosed herein, for example, the compound 7-(3a-amino-1,2,3,7a-tetrahydro-isoindol-2-yl)-1-cyclopropyl-6-fluoro-1,4-dihydro-8-methoxy-4-oxo-3-quinolinecarboxyclic acid, their salts, antibacterial compositions containing them, processes for their preparation, and methods of using them to combat bacterial infections. Disclosed also are intermediates useful in said processes of preparation.

15 Claims, No Drawings

QUINOLONE- AND NAPHTHYRIDONECARBOXYLIC ACID DERIVATIVES

The invention relates to new quinolone- and naphthyridonecarboxylic acid derivatives which are substituted in the 7-position by a diunsaturated bicyclic amine radical, their salts, processes for their preparation, and antibacterial compositions containing these.

The Patent Applications EP 520 240, DE 42 30 804, DE 43 29 600 (Bayer) and JP 4 253 973 (Banyu) already disclose quinolonecarboxylic acids which are substituted in the 7-position by a bicyclic monounsaturated amine radical. These compounds are distinguished by high antibacterial activity. However, they have the disadvantage that they have a high genotoxic potential, which makes their use as medicaments impossible. The invention is therefore based on the object of discovering compounds which, combined with high antibacterial activity, show a decrease in the genotoxic properties.

It has now been found that the Compounds of the formula (I)

T—Q (I)

in which
Q denotes a radical of the formula

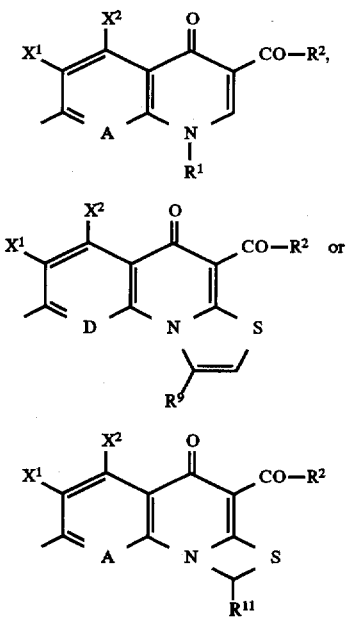

wherein
$R^1$ represents alkyl having 1 to 4 carbon atoms, which is optionally mono- or disubstituted by halogen or hydroxyl, alkenyl-having 2 to 4 carbon atoms, cycloalkyl having 3 to 6 carbon atoms, which is optionally substituted by 1 or 2 fluorine atoms, bicyclo[1.1.1]pent-1-yl, 1,1-dimethylpropargyl, 3-oxetanyl, methoxy, amino, methylamino, dimethylamino, or phenyl which is optionally mono- or disubstituted by halogen, amino or hydroxyl, $R^2$ represents hydroxyl, alkoxy having 1 to 3 carbon atoms, which is optionally substituted by hydroxyl, methoxy, amino or dimethylamino, benzyloxy or (5-methyl-2-oxo-1,3-dioxol-4-yl)-methyloxy, acetoxymethyloxy, pivaloyloxymethyloxy, 5-indanyloxy, phthalidinyloxy, 3-acetoxy-2-oxobutyloxy, nitromethyl or dialkoxycarbonylmethyl having 1 to 2 carbon atoms in each alkyl moiety, $R^9$ represents hydrogen or alkyl having 1 to 3 carbon atoms, which is optionally substituted by methoxy, hydroxy or halogen, $R^{11}$ represents hydrogen, $CH_3$ or $CH_2F$, $X^1$ represents halogen or nitro, $X^2$ represents hydrogen, halogen, amino, hydroxyl, methoxy, mercapto, methyl, halogenomethyl or vinyl, A represents N or $C-R^7$, wherein
$R^7$ represents hydrogen, halogen, $CF_3$, $OCH_3$, $OCHF_2$, $CH_3$, $CN$, $CH=CH_2$ or $C\equiv CH$ or alternatively, together with W, can form a bridge of the structure
—O—$CH_2$—CH—$CH_3$, —S—$CH_2$—$CH_2$—, —*S—$CH_2$—CH—$CH_3$, —*$CH_2$—$CH_2$—CH—$CH_3$ or —*O—$CH_2$—N—$R^8$, the atom marked by * being linked to the carbon atom of A and wherein $R^8$ denotes hydrogen, methyl or formyl, and D represents N or $C-R^{10}$, wherein
$R^{10}$ represents hydrogen, halogen, $CF_3$, $OCH_3$, $OCHF_2$ or $CH_3$ or alternatively, together with $R^9$, can form a bridge of the structure —O—$CH_2$—, —*NH—$CH_2$—, —*N($CH_3$)—$CH_2$—, —*N($C_2H_5$)—$CH_2$—, —N(c—$C_3H_5$)—$CH_2$— or —*S—$CH_2$—, the atom marked by * being linked to the carbon atom of D, and T denotes a radical of the formula

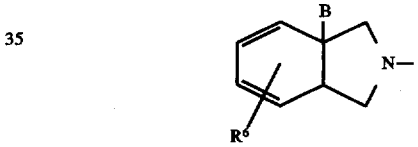

wherein

B represents $(CH_2)_m$—$NR^3R^4$ or $(CH_2)_m$—$OR^5$, wherein m represents 0 or 1,
$R^3$ represents hydrogen, methyl or alkoxycarbonyl having 1 to 4 carbon atoms in the alkyl moiety,
$R^4$ represents hydrogen or methyl and
$R^5$ represents hydrogen or methyl and
$R^6$ represents hydrogen or methyl, and their pharmaceutically utilizable hydrates and acid addition salts and also the alkali metal, alkaline earth metal, silver and guanidinium salts of the underlying carboxylic acids have, combined with good tolerability, high antibacterial action, in particular against gram-positive bacteria.

Preferred compounds of the formula (I) are those in which
Q denotes a radical of the formula

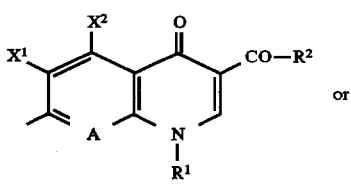

3

-continued

[Chemical structure showing pyridinone with X¹, X², CO-R², D, N, S, R⁹ substituents]

wherein $R^1$ represents alkyl having 1 to 4 carbon atoms, which is optionally mono- or disubstituted by halogen, alkenyl having 2 to 3 carbon atoms, cycloalkyl having 3 or 4 carbon atoms, which is optionally substituted by 1 fluorine atom, bicyclo[1.1.1]pent-1-yl, 1,1-dimethylpropargyl, 3-oxetanyl, methylamino, or phenyl which is optionally mono- or disubstituted by fluorine, amino or hydroxyl, $R^2$ represents hydroxyl, alkoxy having 1 to 2 carbon atoms, benzyloxy or (5-methyl-2-oxo-1,3-dioxol-4-yl)-methoxy, $R^9$ represents hydrogen or alkyl having 1 to 2 carbon atoms, which is optionally mono- to trisubstituted by fluorine, $X^1$ represents fluorine or chlorine, $X^2$ represents hydrogen, halogen, amino, methyl, trifluoromethyl or vinyl, A represents N or C—$R^7$, wherein
  $R^7$ represents hydrogen, halogen, $CF_3$, $OCH_3$, $OCHF_2$, $CH_3$, CN, $CH=CH_2$ or $C≡CH$ or alternatively, together with $R^1$, can form a bridge of the structure —*O—CH$_2$—CH—CH$_3$, —*S—CH$_2$—CH$_2$—, —*CH$_2$—CH$_2$—CH—CH$_3$ or —*O—CH$_2$N—$R^8$, the atom marked by * being linked to the carbon atom of A and wherein
  $R^8$ denotes hydrogen or methyl,
and D represents N or C—$R^{10}$, wherein
  $R^{10}$ represents hydrogen, fluorine, chlorine, $CF_3$, $OCH_3$ or $CH_3$ or alternatively, together with $R^9$, can form a bridge of the structure —O—CH$_2$—, —*N(CH$_3$)—CH$_2$—, —*N(C$_2$H$_5$)—CH$_2$—, —*N(c—C$_3$H$_5$)—CH$_2$— or —*S—CH$_2$—, the atom marked by * being linked to the carbon atom of D, and T denotes a radical of the formula

[Chemical structure with B, R⁶, N— substituents]

wherein

B represents —NR³R⁴ or —OH, wherein
  $R^3$ represents hydrogen or methyl,
  $R^4$ represents hydrogen or methyl and
$R^6$ represents hydrogen and their pharmaceutically utilizable hydrates and acid addition salts and also the alkali metal, alkaline earth metal, silver and guanidinium salts of the underlying carboxylic acids.

Particularly preferred compounds of the formula (I) are those in which

4

Q denotes a radical of the formula

[Chemical structure with X¹, X², CO-R², A, N, R¹]

or

[Chemical structure with X¹, X², CO-R², D, N, S, R⁹]

wherein $R^1$ represents alkyl having 1 to 4 carbon atoms, which is optionally mono- or disubstituted by fluorine, vinyl, cyclopropyl which is optionally substituted by 1 fluorine atom, or phenyl which is optionally mono- or disubstituted by fluorine, $R^2$ represents hydroxyl, alkoxy having 1 to 2 carbon atoms or (5-methyl-2-oxo-1,3-dioxol-4-yl)-methoxy, $R^9$ represents hydrogen or methyl which is optionally mono- to trisubstituted by fluorine, $X^1$ represents fluorine, $X^2$ represents hydrogen, fluorine, amino, methyl or vinyl, A represents N or C—$R^7$, wherein
  $R^7$ represents hydrogen, fluorine, chlorine, bromine, $CF_3$, $OCH_3$, $OCHF_2$, $CH_3$, CN, $CH=CH_2$ or $C≡CH$ or alternatively, together with $R^1$, can form a bridge of the structure —*O—CH$_2$—CH—CH$_3$ or —*O—CH$_2$—N—$R^8$, the atom marked by * being linked to the carbon atom of A and wherein
  $R^8$ denotes hydrogen or methyl,
and D represents N or C—$R^{10}$, wherein
  $R^{10}$ represents hydrogen, fluorine, chlorine or $OCH_3$ or alternatively, together with $R^9$, can form a bridge of the structure —*O—CH$_2$—, —*N(CH$_3$)—CH$_2$—, —*N(C$_2$H$_5$)—CH$_2$— or —*S—CH$_2$—, the atom marked by * being linked to the carbon atom of D, and T denotes a radical of the formula

[Chemical structure with B, R⁶, N— substituents]

wherein

B represents $NH_2$ and
$R^6$ represents hydrogen, and their pharmaceutically utilizable hydrates and acid addition salts and also the alkali metal, alkaline earth metal, silver and guanidinium salts of the underlying carboxylic acids.

It has furthermore been found that the compounds of the formula (I) are obtained on reaction of compounds of the formula (II)

Y—Q (II)

in which
Q has the meaning indicated above and
Y represents a leaving group such as halogen, in particular fluorine or chlorine,
with compounds of the formula (III)

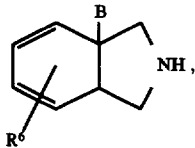

in which
B and $R^6$ have the meanings indicated above,
if appropriate in the presence of acid scavengers and, if appropriate, protective groups present are removed.

If, for example, 6,7-difluoro-1-cyclopropyl-1,4-dihydro-8-methoxy-4-oxo-3-quinolinecarboxylic acid and 1,2,3,7a-tetrahydro-isoindol-3a-ylamine are used as starting substances, the course of the reaction can be shown by the following equation:

DABCO=1,4-diazabicyclo[2.2.2]octane

The compounds of the formula (II) used as starting compounds are known or can be prepared by known methods. They can optionally be employed either as racemic or as enantiomerically pure compounds. In the case of lack of reactivity, the compounds of the formula (II) can also be employed as boron chelates. Examples which may be mentioned are:

7-Chloro-1-cyclopropyl-6-fluoro-1,4-dihydro-4-oxo-3-quinolinecarboxylic acid, 1-cyclopropyl-6,7-difluoro-1,4-dihydro-4-oxo-3-quinolinecarboxylic acid, 6-chloro-1-cyclopropyl-7,8-difluoro-1,4-dihydro-4-oxo-3-quinolinecarboxylic acid, 8-chloro-1-cyclopropyl-6,7-difluoro-1,4-dihydro-4-oxo-3-quinolinecarboxylic acid, 1-cyclopropyl-6,7,8-trifluoro-1,4-dihydro-4-oxo-3-quinolinecarboxylic acid, 5-bromo-1-cyclopropyl-6,7,8-trifluoro-1,4-dihydro4-oxo-3-quinolinecarboxylic acid, 5-bromo-1-(2,4-difluorophenyl)-6,7,8-trifluoro-1,4-dihydro-4-oxo-3 -quinolinecarboxylic acid, 1-cyclopropyl-6,7-difluoro-1,4-dihydro-8-methyl-4-oxo-3-quinolinecarboxylic acid, 6,7-difluoro-1-ethyl-1,4-dihydro-4-oxo-4-oxo-3-quinolinecarboxylic acid, 7-chloro-6-fluoro-1-ethyl-1,4-dihydro-4-oxo-3-quinolinecarboxylic acid, 7-chloro-6-fluoro-1,4-dihydro-1-(2-hydroxyethyl)4-oxo-3-quinolinecarboxylic acid, 6,7-difluoro-1-(2-fluoroethyl)-1,4-dihydro-4-oxo-3-quinolinecarboxylic acid, 7-chloro-6-fluoro-1,4-dihydro-1-methoxy-4-oxo-3-quinolinecarboxylic acid, 7-chloro-6-fluoro-1,4-dihydro-1-methylamine-4-oxo-3-quinolinecarboxylic acid, 6,7-difluoro-1,4-dihydro-4-oxo-1-phenyl-3-quinolinecarboxylic acid, 7-chloro-1-cyclopropyl-6-fluoro-1,4-dihydro-4-oxo-1,8-naphthyridine-3-carboxylic acid, 7-chloro-1-cyclopropyl-6-fluoro-1,4-dihydro-4-oxo-1,8-naphthyridine-3-carboxylic acid ethyl ester, 1-cyclopropyl-6,7,8-trifluoro-1,4-dihydro-4-oxo-3-quinolinecarboxylic acid ester, 9,10-difluoro-2,3-dihydro-3-methyl-7-oxo-7H-pyrido-[1,2,3-de][1,4]benzoiazine-6-carboxylic acid, 8,9-difluoro-6,7-dihydro-5-methyl-1-oxo-1H,5H-benzo[i,j]-quinolizine-2-carboxylic acid, 7-chloro-6-fluoro-1-phenyl-1,4-dihydro-1-oxo-1,8-naphthyridine-3-carboxylic acid, ethyl 7-chloro-6-fluoro-1-(4-fluorophenyl)-1,4-dihydro-4-oxo-1,8-naphthyridine-3-carboxylate, 6,7,8-trifluoro-1,4-dihydro-1-methylamino-4-oxo-3-quinolinecarboxylic acid, 1-amino-6,7,8-trifluoro-1,4-dihydro-4-oxo-3-quinolinecarboxylicacid, 6,7,8-trifluoro-1,4-dihydro-1-dimethylamino-4-oxo-3-quinolinecarboxylic acid, 6,7-difluoro-1-(4-fluorophenyl)-1,4-dihydro-8-methyl-4-oxo-3-quinolinecarboxylic acid, 7-chloro-6-fluoro-1-(4-fluorophenyl)-1,4-dihydro-4-oxo-3-quinolinecarboxylicacid, 7-chloro-6-fluoro-1-(2,4-difluorophenyl)-1,4-dihydro-4-oxo- 3-quinolinecarboxylic acid, 6,7,8-trifluoro-1-(4-fluorophenyl)-1,4-dihydro-4-oxo-3-quinolinecarboxylic acid, 1-cyclopropyl-6,7-difluoro-1,4-dihydro-5-methyl-4-oxo-3-quinolinecarboxylic acid, 7-chloro-1-cyclopropyl-6-fluoro-1,4-dihydro-5-methyl-4-oxo-1,8-naphthyridine-3-carboxylic acid, 7-chloro-6-fluoro-1-(2,4-difluorophenyl)-1,4-dihydro-5-methyl-4-oxo-1,8-naphthyridine-3-carboxylic acid, 6,7-difluoro-1,4-dihydro-1-(3-oxetanyl)-4-oxo-3-quinolinecarboxylic acid, 6,7,8-trifluoro-1,4-dihydro-1-(3-oxetanyl)-4-oxo-3-quinolinecarboxylic acid, 1-(bicyclo[1.1.1]pent-1-yl)-6,7,8-trifluoro-1,4-dihydro-4-oxo-3-quinolinecarboxylic acid, 7-chloro-1-(1,1-dimethylpropargyl)-6-fluoro-1,4-dihydro-4-oxo-1,8-naphthyridine-3-carboxylic acid, 6,7,8-trifluoro-1-(2,4-difluorophenyl)-1,4-dihydro-4-oxo-3-quinolinecarboxylic acid, 6,7,8-trifluoro-1,4-dihydro-4-oxo-1-phenyl-3-quinolinecarboxylic acid, 7-chloro-1-ethyl-6-fluoro-1,4-dihydro-4-oxo-1,8-naphthridine-3-carboxylic acid, 6,7-difluoro-1,4-dihydro4-oxo-1-vinyl-3-quinolinecarboxylic acid, 1-cyclopropyl-5,6,7,8-tetrafluoro-1,4-dihydro-4-oxo-3-quinolinecarboxylic acid, 5-amino-1-cyclopropyl-6,7,8-tdfluoro-1,4-dihydro-4-oxo-3-quinolinecarboxylic acid, 1-cyclopropyl-6,7,8-trifluoro-1,4-dihydro-5-hydroxy-4-oxo-3-quinolinecarboxylic acid, 1-cyclopropyl-6,7-difluoro-1,4-dihydro-8-methoxy-4-oxo-3-quinolinecarboxylic acid, ethyl 7-chloro-1-(2,4-difluorophenyl)-6-fluoro-1,4-dihydro-4-oxo-1,8-naphthyridine-3-carboxylate, 1-cyclopropyl-6,7-difluoro-1,4-dihydro-4-oxo-8-vinyl-3-quinolinecarboxylic acid, 1-cyclopropyl-8-ethinyl-6,7-difluoro-1,4-dihydro-4-oxo-3-quinolinecarboxylic acid, 9,10-difluoro-3-methyl-7-oxo-2,3-dihydro-7H-pyrido[1,2,3-d,e][1,3,4]benzoiadiazine-6-carboxylic acid, 8-amino-9,10-difluoro-3-methyl-7-oxo-2,3-dihydro-7H-pyrido[1,2,3-d,e][1,3,4]benzoxadiazine-6-carboxylic acid, 7,8-difluoro-5-oxo-9,1-[(N-methylimino)methano]-SH-thiazolo[3,2-a]-quinoline-4-carboxylic acid, 7,8-difluoro-5-oxo-9,1-[(N-ethylimino)methano]-5H-thiazolo[3,2-a]-quinoline-4-carboxylic acid, 7,8-difluoro-5-oxo-9,1 -(epoxymethano)-SH-thiazolo[3,2-a]-quinoline-4-carboxylic acid, 7,8-difluoro-5-oxo-9,1 -(epithiomethano)-5H-thiazolo[3,2-a]-quinoline-4-carboxylic acid, 7,8-difluoro-1-methyl-5-oxo-SH-thiazolo[3,2-a]-quinoline-4-carboxylic acid, 8-bromo-6,7-difluoro-1-(cis-2-fluorocyclopropyl)-1,4-dihydro-4-oxo-3-quinolinecarboxylic acid, 8-chloro-6,7-difluoro-1-(cis-2-fluorocyclopropyl)-1,4-dihydro-4-oxo-3-quinolinecarboxylic acid, 6,7-difluoro-1-(cis-2-fluorocydopropyl)-1,4-dihydro-4-oxo-3-quinolinecarboxylic acid, 6,7,8-trifluoro-1-(cis-2-fluorocyclopropyl)-1,4-dihydro-4-oxo-3-quinolinecarboxylic acid, 5,6,7,8-tetrafluoro-1-(cis-2-fluorocyclopropyl)-1,4-dihydro-oxo-3-quinolinecarboxylic acid, 6, 7-difluoro-1-(cis- 2-fluorocyclopropyl)-1,4-dihydro-8-methyl-4-oxo-3-quinolinecarboxylic acid, 8-ethinyl-6,7-difluoro-1-(cis-2-fluorocyclopropyl)-1,4-dihydro4oxo-3-quinolinecarboxylic acid, 6,7-difluoro-1-(cis-2-fluorocyclopropyl)-1,4-dihydro-4-oxo-8-trifluoromethyl-3-quinolinecarboxylic acid, 6,7-difluoro-1-(eis-2-fluorocyclopropyl)-8-difluoromethoxy-1,4-dihydro-4-oxo-3-quinolinecarboxylic acid, 6,7-difluoro-1-(cis-2-fluorocyclopropyl)-1,4-dihydro-8-methoxy-4-oxo-3- quinolinecarboxylic acid, 6,7-difluoro-1-(cis-2-fluorocyclopropyl)-1,4-dihydro-5-methyl-4-oxo-3-quinolinecarboxylic acid, 5-amino-6,7,8-trifluoro-1-(cis-2-fluorocyclopropyl)-1,4-dihydro-4-oxo-3-quinolinecarboxylic acid, 8-bromo-6, 7-difluoro-1-[(1R, 2S)-2-fluorocyclopropyl]-1,4-dihydro-4-oxo-3-quinolinecarboxylic acid, 8-chloro-6,7-difluoro-1-[(1R,2S)-2-fluorocyclopropyl]-1,4-dihydro4oxo-3-quinolinecarboxylic acid, 6,7-difluoro-1-[(1R,2S)-2-fluorocyclopropyl]-1,4-dihydro-4-oxo-3-quinolinecarboxylic acid, 6,7,8-trifluoro-1-[(1R,2S)-2-fluorocyclopropyl]-1,4-dihydro-4-oxo-3-quinolinecarboxylic acid, 5,6,7,8-tetrafluoro-1[(1R,2S)-2-fluorocyclopropyl]-1,4-dihydro-4-oxo-3-quinolinecarboxylic add, 6,7-difluoro-1-[(1R,2S)-2-fluorocyclopropyl]-1,4-dihydro-8-methyl-4-oxo-3-quinolinecarboxylic acid, 8-ethinyl-6,7-difluoro-1-[( 1R, 2S)-2-fluorocyclopropyl]-1,4-dihydro-4-oxo-3-quinolinecarboxylic acid, 6,7-difluoro-1-[(1R,2S)-2-fluorocyclopropyl]-1,4-dihydro-4-oxo-8-trifluoromethyl-3-quinolinecarboxylic acid, 6,74-fluoro-1-[(1R,2S)-2-fluorocyclopropyl]-8-difluoromethoxy-1,4-dihydro4-oxo-3-quinolinecarboxylic acid, 6,7-difluoro-1-[(1R, 2S)-2-fluorocyclopropyl]-1,4-dihydro-8-methoxy-4-oxo-3-quinolinecarboxylic acid, 6,7-difluoro-1-[(1R,2S)-2-fluorocyclopropyl]-1,4-dihydro-5-methyl-4-oxo-3-quinolinecarboxylic acid, 5-amino-6,7,8-trifluoro-1-[(1R, 2S)-2-fluorocyclopropyl]-1,4-dihydro-4-oxo-3-quinolinecarboxylic acid, 6,7-difluoro-4-oxo-4H-[1,3]thiazeto[3,2-a]quinoline-3-carboxylic acid, 6,7-difluoro-1-methyl-4-oxo4H-[1,3]thiazeto[3,2-a]quinoline23-carboxylic acid, 6,7-difluoro-1-fluoromethy14-oxo4H-[1,3]thiazeto[3,2-a]quinoline-3-carboxylic acid, 1-cyclopropyl-6,7-difluoro-1,4-dihydro-8-methyl-4-oxo-3-quinolinecarboxylic acid —B(O—CO—CH$_3$)$_2$ chelate.

The bicyclic amines of the formula (III) required as starting compounds are new. They can be prepared by the methods shown in scheme 1: Starting from an alkyl 2,5-dihydropyrrolecarboxylate (1), the Dieis-Alder adducts (2) or (3) can be synthesized using suitable dienes. Instead of dienes, suitable diene synthons, such as, for example α-pyrone, can also be used. From (2), by addition of bromine in inert solvents and subsequent dehydrobromination with strong bases such as, for example, potassium tertbutoxide, 1,5-diazabicyclo[4.3.0]non-5-ene, 1,8-diazabicyclo[5.4.0]undec-7-ene or ethyl-diisopropylamine the diene (4) can be synthesized, which can also be obtained by acid treatment from the intermediate (3). The alkyl dienecarboxylate (4) is hydrolysed to the carboxylic acid which can be degraded to the amine (6), for example by means of Hoffmann or Curtius degradation via the urethane (5) as intermediate. Furthermore, the urethane (5) can be selectively alkylated on the urethane nitrogen to give the alkylurethane (7) into which, after selective removal of the urethane group, a second alkyl group can optionally be introduced and thereby converted into (8). By reduction of the diene carboxylic acid ester (4) with complex hydrides, the hydroxymethyl compound (12) can be synthesized via the intermediate (9). Furthermore, the amines of the structure (11) can be prepared from (9) via amines of the structure (10) after activation of the hydroxy group, for example by conversion into an O-tosylate or an O-mesylate and subsequent nucleophilic substitution with amines or azides, which must then be reduce&. Instead of the alkyl carboxylate (1), an analogous 2,5-dihydropyrrole-3-carbonitrile can also be employed for the synthesis, from which 3a-aminomethyl-1, 2,3,7a-tetrahydro-isoindole can be prepared, for example by a similar reaction sequence (Dieis-Alder reaction, reduction).

The intermediates of the structures (6), (8), (11) and (12) correspond to the general formula (III).

1-Amino-8-azabicyclo[4.3.0]nona-2,4-diene can also be prepared by reacting methyl 8-azabicyclo[4.3.0]nona-2,4-diene-1-carboxamide-8-carboxylate by means of a Hoffmann degradation, for example with sodium hypochlorite, sodium hypobromite or iodosobenzene to give methyl 1-amino-8-azabicyclo[4.3.0]nona-2,4-diene-8-carboxylate and then removing the carbamate protective group by treatment with acids or bases.

Scheme 1:
Synthesis of 3a-substituted 1,2,3,7a-tetrahydroisoindoles (R = C$_{1-3}$-alkyl, R' = benzyl, CO—C$_{1-3}$-alkyl, CO$_2$—C$_{1-3}$-alkyl, R" = Si(CH$_3$)$_3$, R'" = C$_{1-4}$-alkyl)

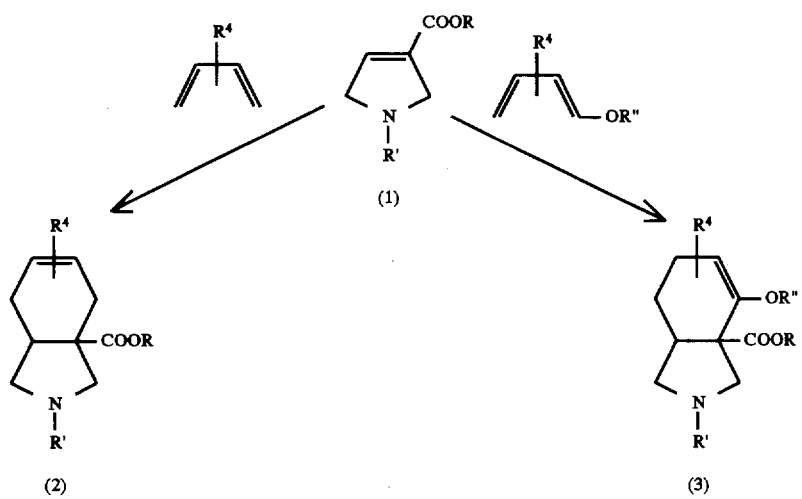

Scheme 1:
Synthesis of 3a-substituted 1,2,3,7a-tetrahydroisoindoles

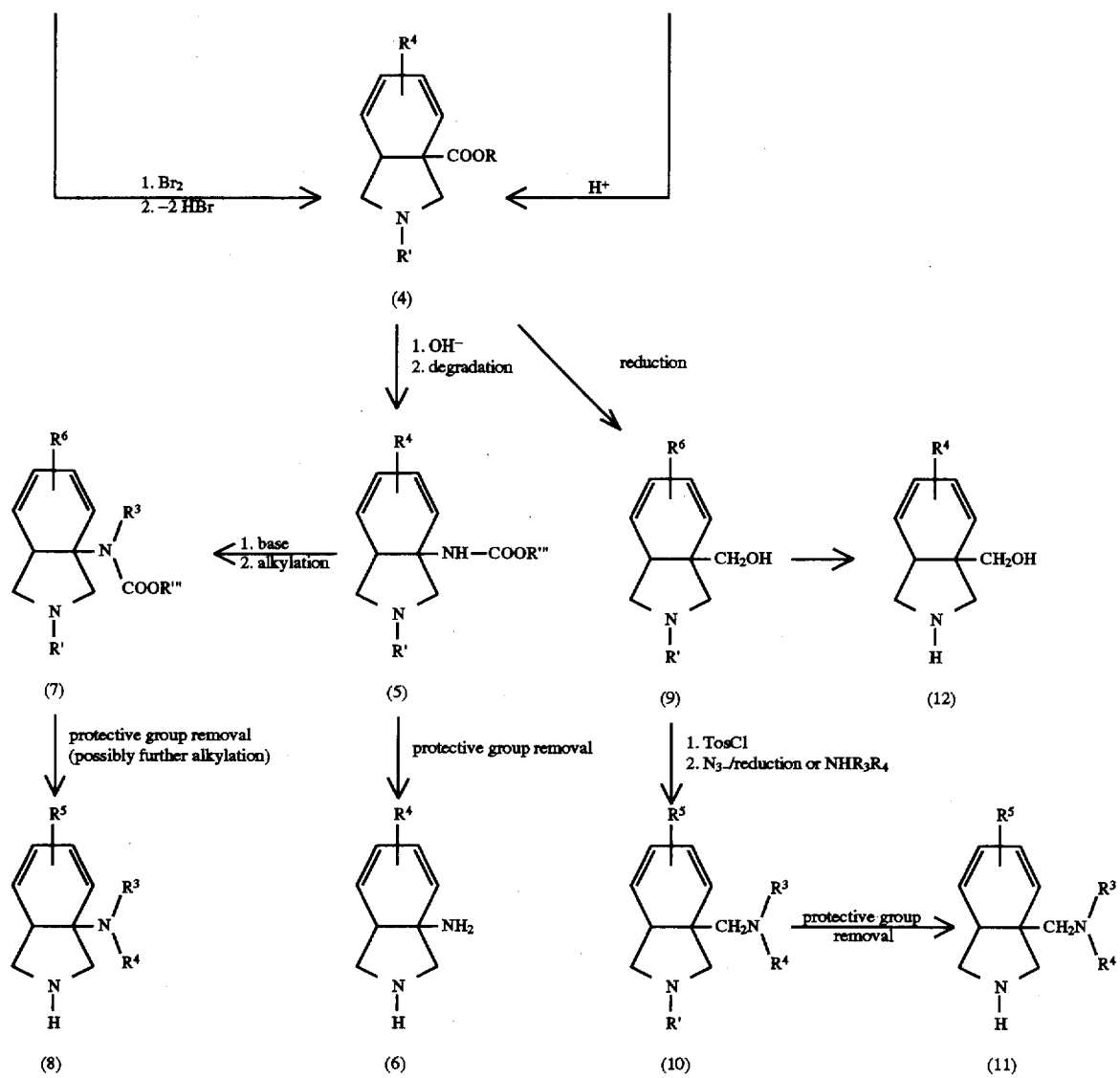

Examples of diunsaturated bicyclic amines of the formula (III) which may be mentioned are:

1,2,3,7a-Tetrahydro-isoindol-3a-ylamine, 4-methyl-1,2,3, 7a-tetrahydro-isoindol- 3a-ylamine, 5-methyl-1,2,3,7a-tetrahydro-isoindol-3a-ylamine, 6-methyl-1,2,3,7a-tetrahydro-isoindol-3a-ylamine, 7-methyl-1,2,3,7a-tetrahydro-isoindol-3a-ylamine, 3a-methylamino-1,2,3,7a-tetrahydro-isoindole, 3a-dimethylamino-1,2,3,7a-tetrahydro-isoindole, 3a-tert-butoxycarbonylamino-1,2,3, 7a-tetrahydro-isoindole, 3a-aminomethyl-1,2,3,7a-tetrahydro-isoindole, 3a-methylaminomethyl-1,2,3,7a-tetrahydro-isoindole, 3a-dimethylaminomethyl-1,2,3,7a-tetrahydro-isoindole,3a-hydroxy-1,2,3,7a-tetrahydro-isoindole, 3a-hydroxymethyl-1,2,3,7a-tetrahydro-isoindole.

The enantiomerically pure starting compounds of the formula (III) can be prepared by the following processes:

1. The racemic bicyclic amines (III) can be reacted with enantiomerically pure acids, for example carboxylic acids or sulphonic acids such as N-acetyl-L-glutamic acid, N-benzoyl-L-alanine, 3-bromo-camphor-9-sulphonic acid, camphor-3-carboxylic acid, cis-camphoric acid, camphor-10-sulphonie acid, O,O-dibenzoyltartaric acid, D- or L-tartaric acid, mandelic acid, α-methoxy-phenylacetic acid, 1-phenyl-ethanesulphonic acid or a-phenyl-succinic acid to give a mixture of the diastereomeric salts, which can then be separated by fractional crystallization to give the diastereomerically pure salts (see P. Neroran, Optical Resolution Procedures for Chemical Compounds, Volume 1 ). The enantiomerically pure amines can be liberated by treatment of these salts with alkali metal or alkaline earth metal hydroxides.

2. In a similar manner to that described under 1., separation of the racemates of the basic intermediates (see Scheme 1), racemic bicyclic amines, can be carried out using the abovementioned enantiomerically pure acids.

3. Both the racemic amines (III) and the intermediates shown in Scheme 1 can be separated chromatographically, optionally after acylation, by means of chiral support materials (see, for example, G. Blaschke, Angew. Chem. 92, 14 [1980]).

4. The racemic amines (III) can also be converted by chemical linkage with chiral acyl radicals into diastereomer mixtures which can be separated by distillation, crystallization or chromatography into the diastereomerically pure acyl derivatives from which the enantiomerically pure amines can be isolated by hydrolysis. Examples of reagents for linkage with chiral acyl radicals are: α-methoxy-α-trifluoromethyl-phenylacetyl chloride, menthyl isocyanate, D- or L-α-phenyl-ethyl isocyanate, menthyl chloroformate and camphor-10-sulphonyl chloride.

5. In the come of the synthesis of the bicyclic amines (III), instead of achiral protective groups, chiral protective groups can also be introduced. Diastereomer mixtures which can be separated can be obtained in this manner. For example, in the synthesis of the intermediate (4) in Scheme I the benzyl radical can be replaced by the R- or S-configured α-phenylethyl radical, or the alcohol component of the ester (4) by an enantiomerically pure alcohol, such as, for example, menthol or pantolactone.

The reaction of (II) with (III), in which the compounds (III) can also be employed in the form of their salts, such as, for example, the hydrochlorides, is preferably carded out in a diluent such as dimethyl sulphoxide, N,N-dimethylformamide, N-methylpyrrolidone, hexamethylphosphoramide, sulpholane, acetonitrile, water, an alcohol such as methanol, ethanol, N-propanol or isopropanol, glycol monomethyl ether or pyridine. Mixtures of these diluents can also be used.

The acid binders used can be all customary inorganic and organic acid binders. These preferably include the alkali metal hydroxides, alkali metal carbonates, organic amines and amidines. The following may be specifically mentioned as particularly suitable: triethylamine, 1,4-diazabicyclo [2.2.2]octane (DABCO), 1,8-diazabicyclo[5.4.0]undec-7-ene (DBU) or excess amine (III).

The reaction temperatures can be varied within a relatively wide range. In general, the reaction is carried out between about 20° and 200° C., preferably between 80° and 160° C.

The reaction can be carried out at normal pressure, but also at elevated pressure. In general, it is carried out at pressures between about 1 and 100 bar, preferably between 1 and 10 bar.

When carrying out the process according to the invention, 1 to 15 mol, preferably 1 to 5 mol, of the compound (III) are employed relative to 1 mol of the compound (II).

Free amino groups can be protected during the reaction by a suitable amino protective group, such as, for example, by the tert-butoxycarbonyl radical or an azomethine protective group, and liberated again after completion of the reaction.

The compounds of the formula (I) according to the invention in which $R^2$ represents $CH_2NO_2$ or dialkoxycarbonylmethyl can also be obtained by reacting a compound of the formula (I) in which $R^2$ represents OH with an activating agent such as carbonyl-diimidazole in a solvent such as tetrahydrofuran, dichloromethane or chloroform and then reacting with a CH-acidic compound such as nitromethane or dialkyl malonate. This reaction is preferably carried out in a solvent such as tetrahydrofuran in the presence of a base (sodium hydride, potassium carbonate or sodium carbonate).

The compounds of the formula (I) according to the invention in which $X^2=NH_2$ are also prepared by reaction of compounds of the formula (I) in which $X^2=F$ with ammonia in polar solvents such as dimethyl sulphoxide at temperatures from 50° C. to 120° C. at normal pressure or by heating in an autoclave. Compounds of the formula (I) according to the invention in which A=C—$OCH_3$ are also prepared by reaction of compounds of the formula (I) in which A=C—F with alkali metal methoxides, such as, for example, sodium methoxide, in solvents such as, for example, dimethylformamide, glycol dimethyl ether, dioxane, tetrahydrofuran, dimethyl sulphoxide, hexamethylphosphoramide or alcohols at temperatures from 20° C. to 150° C. When using low-boiling solvents, the reaction can also be carried out under pressure in an autoclave. The reaction can be accelerated by addition of crown ethers, such as, for example, 15-crown-5 or 18-crown-6.

To prepare the esters according to the invention, the underlying carboxylic acid is preferably reacted in excess alcohol in the presence of strong acids, such as sulphuric acid, anhydrous hydrogen chloride, methanesulphonic acid, p-toluenesulphonic acid or acidic ion exchangers., at temperatures from about 20° to 180° C., preferably about 60° to 120° C. The resulting water of reaction can also be removed by azeotropic distillation with chloroform, tetrachloromethane or toluene.

Esters are also advantageously prepared by heating the underlying acid with dimethylformamide dialkyl acetal in a solvent such as dimethylformamide.

The esters used as a prodrug, such as, for example, (5-methyl-2-oxo-1,3-dioxol-4-yl-methyl) ester, are obtained by reaction of an alkali metal salt of the underlying carboxylic acid, which can optionally be protected on the N atom by a protective group, with 4-bromomethyl- or 4-chloromethyl-5-methyl-1,3-dioxol-2-one in a solvent such as dimethylformamide, dimethylacetamide, N-methylpyrrolidone, dimethyl sulphoxide or tetramethylurea at temperatures from about 0° to 100° C., preferably 0° to 50° C.

The acid addition salts of the compounds according to the invention are prepared in a customary manner, for example by dissolving in excess aqueous acid and precipitating the salt using a water-miscible solvent such as methanol, ethanol, acetone or acetonitrile. An equivalent amount of betaine and acid in water can also be lyophilised or can be heated in water or an alcohol such as glycol monomethyl ether and then evaporated to dryness or the precipitated salt can be filtered off with suction. Pharmaceutically utilizable salts are to be understood as meaning, for example, the salts of hydrochloric acid, sulphuric acid, acetic acid, glycolic acid, lactic acid, succinic acid, citric acid, tartaric acid, 2-hydroxyglutaric acid, methanesulphonic acid, 4-toluenesulphonic acid, galacturonic acid, glucuronic acid, 5-oxotetrahydrofuran-2-carboxylic acid, embonic acid, glutamic acid or aspartic acid.

The alkali metal and alkaline earth metal salts of the carboxylic acids according to the invention are obtained, for example, by dissolving the betaine in excess alkali metal or alkaline earth metal hydroxide solution, filtering from undissolved betaine and evaporating to dryness. Pharmaceutically suitable salts are those of sodium, potassium and calcium. The corresponding silver salts are obtained by reaction of an alkali metal or alkaline earth metal salt with a suitable silver salt such as silver nitrate.

Apart from the active compounds mentioned in the examples, the active compounds listed below and the active compounds listed in the tables which follow can also be prepared, which can be present either as racemates or as enantiomerically pure compounds or if appropriate also as diastereomer mixtures or as diastereomerically pure compounds:

8-(3a-Amino-1,2,3,7a-tetrahydro-isoindol-2-yl)-7-fluoro-5-oxo-9,1 -(epoxymethano)-5H-thiazolo[3,2-a]quinoline-4-carboxylic acid, 7-fluoro-8-(3a-methylamino-1,2,3,7a-tetrahydro-isoindol-2-yl)-5-oxo-9, 1-(epoxymethano)-SHthiazolo[3,2-a]quinoline-4-carboxylic acid, 8-(3a-aminomethyl-1,2,3,7a-tetrahydro-isoindol-2-yl)-7-fluoro-5-oxo-9,1-(epoxymethano)-5H-thiazolo[3,2-a]quinoline4carboxylic acid, 7-fluoro-8-(3a-methylaminomethyl-1,2,3,7a-tetrahydro-isoindol-2-yl)-5-oxo-9,1 -(epoxymethano)-5H-thiazolo[3,2-a]quinoline4carboxylic acid, 8-(3a-arnino-1,2,3,7a-tetrahydro-isoindol-2-yl)-7-fluoro-5-oxo-9,1-[(N-methyl-imino)methano]-SH-thiazolo[3,2-a]quinoline-4-carboxylic acid, 7-fluoro-8-(3a-methylamino-1,2,3,7a-tetrahydro-isoindol-2-yl)-5-oxo-9,1-[(N-methyl-imino)methano]-5H-thiazolo[3,2-a]quinoline4carboxylic acid, 8-(3a-aminomethyl-1,2,3,7a-tetrahydro-isoindol-2-yl)-7-fluoro-5-oxo-9,1-[(N-methyl-imino)methano]-5H-thiazolo[3,2-a]quinoline-4-carboxylic add, 7-fluoro-8-(3a-methyl-aminomethyl-1,2,3,7a-tetrahydro-isoindol-2-yl)-5-oxo-9,1-[(N-methyl-imino)methano]-5H-thiazolo[3,2-a]quinoline4-carboxylic acid, 10-(3a-amino-1,2,3,7a-tetrahydro-isoindol-2-yl)-9-fhoro-3-methyl-7-oxo-2,3-dihydro-7H-pyrido[1,2,3-d,e]-[1,3,4]benzoxadiazine-6-carboxylic acid, 9-fluoro-3-methyl-10-(3a-methylamino-1,2,3,7a-tetrahydro-isoindol-2-yl)-7-oxo-2,3-dihydro-7H-pyrido[1,2,3-d,e]-[1,3,4]benzoxadiazine-6-carboxylic acid, 10-(3a-aminomethyl-1,2,3,7a-tetrahydro-isoindol-2-yl)-9-fluoro-3-methyl-7-oxo-2,3-dihydro-7H-pyrido[1,2,3-d,e]-[1,3,4]benzoxadiazine-6-carboxylic acid, 8-amino-10-(3a-amino-1,2,3,7a-tetrahydro-isoindol-2-yl)-9-fluoro-3-methyl-7-oxo-2,3-dihydro-7H-pyrido[1,2,3-d,e][1,3,4]-benzoxadiazine-6-carboxylic acid, 10-(3a-dimethylaminomethyl-1,2,3,7a-tetrahydro-isoindol-2-yl)-9-fluoro-3-methyl-7-oxo-2,3 -dihydro-7H-pyrido[1,2,3 -d,e][1,3,4]-benzoxadiazine-6-carboxylic acid, 9-fluoro-3-methyl-10-(3a-methylamino-1,2,3,7a-tetrahydro-isoindol-2-yl)-7-oxo-2,3-dihydro-7H-pyrido[1,2,3-d,e][1,4]benzoxazine-6-carboxylic acid, 10-(3a-aminomethyl-1,2,3,7a-tetrahydro-isoindol-2-yl)-9-fluoro-3-methyl-7-oxo-2,3-dihydro-7H-pyrido[1,2,3-d,e][1,4]benzoxazine-6-carboxylic acid, 8-amino-10-( 3a-amino-1,2,3,7a-tetrahydro-isoindol-2-yl)-9-fluoro-3-methyl-7-oxo-2,3-dihydro-7H-pyrido[1,2,3-d,e][1,4]benzoxazine-6-carboxylic acid, 10-(3a-amino-5-methyl-1,2,3,7a-tetrahydro-isoindol-2-yl)-9-fluoro-3-methyl-7-oxo-2,3-dihydro-7H-pyrido[1,2,3-d,e][1,4]benzoxazine-6-carboxylic acid, 7-(3a-amino-1,2,3,7a-tetrahydro-isoindol-2-yl)-6- fluoro4-oxo-4H-[1,3 ]thiazeto[3,2-a]quinoline-3-carboxylic acid, 7-(3a-amino-1,2,3,7a-tetrahydro-isoindol-2-yl)-6-fluoro-1-methy14-oxo-4H-[1,3]thiazeto[3,2-a]quinoline-3-carboxylic acid, 7-(3a-amino-1,2,3,7a-tetrahydro-isoindol-2-yl)-6-fluoro-1-fluoromethyl-4-oxo-4H-[1,3]thiazeto[3,2-a]quinoline-3-carboxylic acid, 7-(3a-amino-1,2,3,7a-tetrahydro-isoindol-2-yl)-1-cyclopropyl-6-fluoro-3 -nitroacetyl-4-oxo-1,4-dihydroquinoline, 7-(3a-amino-1,2,3,7a-tetrahydro-isoindol-2-yl)-1-cyclopropyl-6-fluoro-8-methoxy-3-nitroacetyl-4-oxo-1,4-dihydroquinoline, 7-(3a-amino-1,2,3,7a-tetrahydro-isoindol-2-yl)-1-cyclopropyl-6,8-difluoro-3-nitroacetyl-4-oxo-1,4-dihydroquinoline, 7-(3a-amino-1,2,3,7a-tetrahydro-isoindol-2-yl)-1-cyclopropyl-8-chloro-6-fluoro-3-nitroacetyl-4-oxo-1,4-dihydroquinoline, 7-(3a-amino-1,2,3,7a-tetrahydro-isoindol-2-yl)-1-cyclopropyl-3-(diethoxycarbonyl)acetyl-6-fluoro-4-oxo-1,4-dihydroquinoline, 7-(3a-amino-1,2,3,7a-tetrahydro-isoindol-2-yl)-1-cyclopropyl-3-(diethoxycarbonyl)acetyl-6-fluoro-8-methoxy-4-oxo-1,4-dihydroquinoline, 7-(3a-amino-1,2,3,7a-tetrahydro-isoindol-2-yl)-1-cyclopropyl-3-(diethoxycarbonyl)acetyl-6,8-difluoro-4-oxo-1,4-dihydroquinoline, 7-(3a-amino-1,2,3,7a-tetrahydro-isoindol-2-yl)-8-chloro-1-cyclopropyl-3-(diethoxycarbonyl)acetyl-6-fluoro-4-oxo-1,4-dihydroquinoline.

TABLE 1

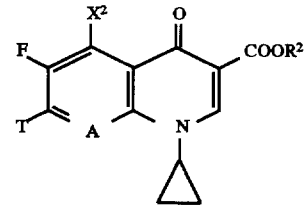

| T* | A | $X^2$ | $R^2$ |
|---|---|---|---|
| $T^I$ | C—H | H | H |
| $T^I$ | C—F | H | H |
| $T^I$ | C—Cl | H | H |
| $T^I$ | C—$CH_3$ | H | H |
| $T^I$ | C—$OCH_3$ | H | H |
| $T^I$ | N | H | H |
| $T^I$ | C—F | F | H |
| $T^I$ | C—F | $NH_2$ | H |
| $T^I$ | C—F | H | $C_2H_5$ |
| $T^I$ | C—Cl | H | $C_2H_5$ |
| $T^I$ | C—C≡CH | H | H |
| $T^I$ | C—CH=$CH_2$ | H | H |
| $T^I$ | C—$OCHF_2$ | H | H |
| $T^I$ | C—$CF_3$ | H | H |
| $T^{II}$ | C—$CH_3$ | F | H |
| $T^{II}$ | C—$CF_3$ | $NH_2$ | H |
| $T^{II}$ | C—$OCH_3$ | H | $C_2H_5$ |

*$T^I$ = 3a-aminomethyl-1,2,3,7a-tetrahydroisoindol-2-yl
$T^{II}$ = 3a-amino-1,2,3,7a-tetrahydroisoindol-2-yl

TABLE 2

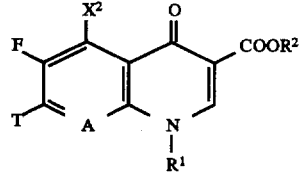

| T* | A | $X^2$ | $R^1$ | $R^2$ |
|---|---|---|---|---|
| $T^I$ | C—H | H | $C(CH_3)_3$ | H |
| $T^{II}$ | N | H | $C(CH_3)_3$ | H |
| $T^I$ | N | H | $C(CH_3)_3$ | H |
| $T^{II}$ | N | $CH_3$ | $C(CH_3)_3$ | H |
| $T^{II}$ | C—F | H | $C(CH_3)_3$ | H |
| $T^I$ | C—H | H | fluoro-tert-butyl | H |
| $T^{II}$ | C—H | H | fluoro-tert-butyl | $C_2H_5$ |
| $T^I$ | N | H | fluoro-tert-butyl | H |
| $T^{II}$ | N | H | fluoro-tert-butyl | H |
| $T^{II}$ | C—$OCH_3$ | H | fluoro-tert-butyl | H |
| $T^I$ | C—H | H | 2,4-difluorophenyl | H |
| $T^{II}$ | C—H | H | 2,4-difluorophenyl | H |
| $T^I$ | C—F | H | 2,4-difluorophenyl | H |
| $T^{II}$ | C—F | H | 2,4-difluorophenyl | H |
| $T^I$ | N | H | 2,4-difluorophenyl | H |
| $T^{II}$ | N | H | 2,4-difluorophenyl | $C_2H_5$ |

*$T^I$ = 3a-aminomethyl-1,2,3,7a-tetrahydroisoindol-2-yl
$T^{II}$ = 3a-amino-1,2,3,7a-tetrahydroisoindol-2-yl

TABLE 3

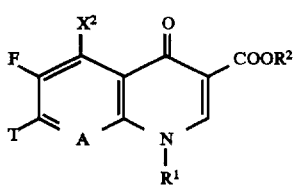

| T* | A | $X^2$ | $R^1$ | $R^2$ |
|---|---|---|---|---|
| $T^I$ | C—H | H | bicyclo[1.1.1]pent-1-yl | H |
| $T^{II}$ | C—H | H | bicyclo[1.1.1]pent-1-yl | H |
| $T^I$ | N | H | bicyclo[1.1.1]pent-1-yl | H |
| $T^{II}$ | N | $CH_3$ | bicyclo[1.1.1]pent-1-yl | H |
| $T^I$ | C—F | H | bicyclo[1.1.1]pent-1-yl | H |
| $T^{II}$ | C—F | H | bicyclo[1.1.1]pent-1-yl | H |
| $T^I$ | C—$OCH_3$ | H | bicyclo[1.1.1]pent-1-yl | H |
| $T^{II}$ | C—$OCH_3$ | H | bicyclo[1.1.1]pent-1-yl | H |
| $T^I$ | C—H | H | 3-oxetanyl | H |
| $T^{II}$ | C—H | H | 3-oxetanyl | H |
| $T^I$ | N | H | 3-oxetanyl | H |
| $T^{II}$ | N | H | 3-oxetanyl | H |
| $T^I$ | C—F | H | 3-oxetanyl | H |
| $T^{II}$ | C—F | H | 3-oxetanyl | H |
| $T^I$ | C—$OCH_3$ | H | 3-oxetanyl | H |
| $T^{II}$ | C—$OCH_3$ | H | 3-oxetanyl | H |
| $T^{II}$ | C—H | H | 4-fluorophenyl | $C_2H_5$ |

*$T^I$ = 3a-aminomethyl-1,2,3,7a-tetrahydroisoindol-2-yl
$T^{II}$ = 3a-amino-1,2,3,7a-tetrahydroisoindol-2-yl

TABLE 4

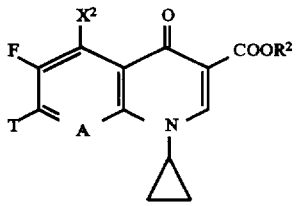

| T* | A | $X^2$ | $R^2$ |
|---|---|---|---|
| $T^{III}$ | C—H | H | H |
| $T^{IV}$ | C—H | H | H |
| $T^{III}$ | C—F | H | H |
| $T^{IV}$ | C—F | H | H |
| $T^{III}$ | C—Cl | H | H |
| $T^{IV}$ | C—Cl | H | H |
| $T^{III}$ | C—$OCH_3$ | H | H |
| $T^{IV}$ | C—$OCH_3$ | H | H |
| $T^{III}$ | C—$CHF_2$ | H | H |
| $T^{IV}$ | C—$CHF_2$ | H | H |
| $T^{III}$ | C—$CF_3$ | H | H |
| $T^{IV}$ | C—$CF_3$ | H | H |
| $T^{III}$ | C—$CH_3$ | H | H |
| $T^{IV}$ | C—$CH_3$ | H | H |
| $T^{III}$ | C—CH=$CH_2$ | H | H |
| $T^{IV}$ | C—CH=$CH_2$ | H | H |
| $T^{III}$ | C—C≡CH | H | H |
| $T^{IV}$ | C—C≡CH | H | H |

*$T^{III}$ = 3a-methylamino-1,2,3,7a-tetrahydroisoindol-2-yl
$T^{IV}$ = 3a-dimethylamino-1,2,3,7a-tetrahydroisoindol-2-yl

TABLE 5

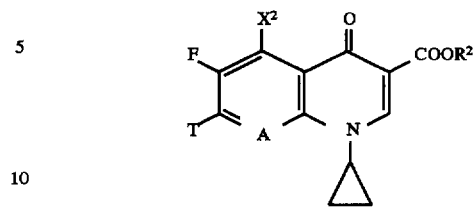

| T* | A | $X^2$ | $R^2$ |
|---|---|---|---|
| $T^{III}$ | C—F | $NH_2$ | H |
| $T^{IV}$ | C—F | $NH_2$ | H |
| $T^{III}$ | C—F | F | H |
| $T^{IV}$ | C—F | F | H |
| $T^{III}$ | N | H | H |
| $T^{IV}$ | N | H | H |
| $T^{III}$ | C—$OCH_3$ | H | $C_2H_5$ |
| $T^{IV}$ | C—$OCH_3$ | H | $C_2H_5$ |
| $T^{III}$ | C—$OCH_3$ | H | (5-methyl-2-oxo-1,3-dioxol-4-yl)-methyl |
| $T^{IV}$ | C—$OCH_3$ | H | (5-methyl-2-oxo-1,3-dioxol-4-yl)-methyl |
| $T^I$ | C—$OCH_3$ | H | (5-methyl-2-oxo-1,3-dioxol-4-yl)-methyl |
| $T^{II}$ | C—$OCH_3$ | H | (5-methyl-2-oxo-1,3-dioxol-4-yl)-methyl |
| $T^{III}$ | N | $CH_3$ | H |
| $T^{IV}$ | N | $CH_3$ | H |
| $T^I$ | C—H | $CH_3$ | H |
| $T^{II}$ | C—H | $CH_3$ | H |
| $T^{III}$ | C—H | $CH_3$ | H |
| $T^{IV}$ | C—H | $CH_3$ | H |

*$T^I$ = 3a-aminomethyl-1,2,3,7a-tetrahydroisoindol-2-yl
$T^{II}$ = 3a-amino-1,2,3,7a-tetrahydroisoindol-2-yl
$T^{III}$ = 3a-methylamino-1,2,3,7a-tetrahydroisoindol-2-yl
$T^{IV}$ = 3a-dimethylamino-1,2,3,7a-tetrahydroisoindol-2-yl

TABLE 6

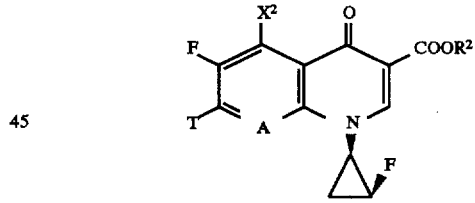

| T* | A | $X^2$ | $R^2$ |
|---|---|---|---|
| $T^I$ | C—H | H | H |
| $T^I$ | C—F | H | H |
| $T^I$ | C—Cl | H | H |
| $T^I$ | C—$CH_3$ | H | H |
| $T^I$ | C—$OCH_3$ | H | H |
| $T^I$ | N | H | H |
| $T^I$ | C—F | F | H |
| $T^I$ | C—F | $NH_2$ | H |
| $T^I$ | C—F | H | $C_2H_5$ |
| $T^I$ | C—Cl | H | $C_2H_5$ |
| $T^{II}$ | C—H | H | H |
| $T^{II}$ | C—F | H | H |
| $T^{II}$ | C—Cl | H | $C_2H_5$ |
| $T^{II}$ | C—$CH_3$ | H | H |
| $T^{II}$ | C—$OCH_3$ | H | H |
| $T^{II}$ | N | H | H |
| $T^{II}$ | C—F | F | H |

*$T^I$ = 3a-aminomethyl-1,2,3,7a-tetrahydroisoindol-2-yl
$T^{II}$ = 3a-amino-1,2,3,7a-tetrahydroisoindol-2-yl

TABLE 7

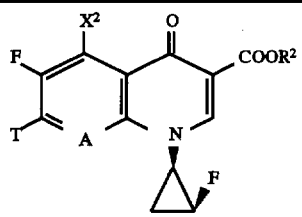

| T* | A | X² | R² |
|---|---|---|---|
| T^III | C—H | H | H |
| T^III | C—F | H | H |
| T^III | C—Cl | H | H |
| T^III | C—CH₃ | H | H |
| T^III | C—OCH₃ | H | H |
| T^III | N | H | H |
| T^III | C—F | F | H |
| T^III | C—F | NH₂ | H |
| T^III | C—F | H | C₂H₅ |
| T^III | C—Cl | H | C₂H₅ |
| T^IV | C—H | H | H |
| T^IV | C—F | H | H |
| T^IV | C—Cl | H | H |
| T^IV | C—CH₃ | H | H |
| T^IV | C—OCH₃ | H | H |
| T^IV | N | H | H |
| T^IV | C—F | F | H |

*T^III = 3a-methylamino-1,2,3,7a-tetrahydroisoindol-2-yl
T^IV = 3a-dimethylamino-1,2,3,7a-tetrahydroisoindol-2-yl

TABLE 8

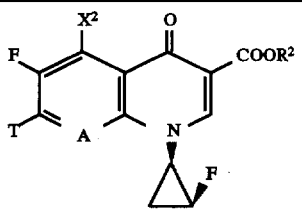

| T* | A | X² | R² |
|---|---|---|---|
| T^V | C—H | H | H |
| T^V | C—F | H | H |
| T^V | C—Cl | H | H |
| T^V | C—CH₃ | H | H |
| T^V | C—OCH₃ | H | H |
| T^V | N | H | H |
| T^V | C—F | F | H |
| T^V | C—F | NH₂ | H |
| T^V | C—F | H | C₂H₅ |
| T^V | C—Cl | H | C₂H₅ |
| T^VI | C—H | H | H |
| T^VI | C—F | H | H |
| T^VI | C—Cl | H | H |
| T^VI | C—CH₃ | H | H |
| T^VI | C—OCH₃ | H | H |
| T^VI | N | H | H |
| T^VI | C—F | F | H |

*T^V = 3a-methylaminomethyl-1,2,3,7a-tetrahydroisoindol-2-yl
T^VI = 3a-ethylaminomethyl-1,2,3,7a-tetrahydroisoindol-2-yl The compounds according to the invention have strong antibiotic activity and, combined with low toxicity, exhibit a broad antibacterial spectrum against gram-positive and gram-negative bacteria, especially also against those which are resistant to various antibiotics, such as, for example, penicillins, cephalosporins, aminoglycosides, sulphonamides, tetracyclines as well as to commercially available quinolones. The compounds according to the invention are particularly distinguished in that, in comparison with the compounds of the prior art, they have fewer interactions with mammalian DNA.

These useful properties make possible their use as chemotherapeutic active compounds in medicine and in veterinary medicine. They can furthermore be used as substances for the preservation of inorganic and organic materials, for example of polymers, lubricants, colorants, fibres, leather, paper and wood, of foodstuffs and of water.

The compounds according to the invention are active against a very wide spectrum of microorganisms. Gram-negative and gram-positive bacteria and bacteria-like organisms can be controlled using them and the diseases caused by these pathogens can be prevented, ameliorated and/or cured.

The compounds according to the invention are distinguished by an increased action on dormant microorganisms. In the case of dormant bacteria, i.e. bacteria which exhibit no detectable growth, the compounds have strong bactericidal activity. This relates not only to the amount to be employed, but also to the rate of destruction. Such results could be observed with gram-positive and gram-negative bacteria, in particular with Staphylococcus aureus, Pseudomonas aeruginosa, Enterococcus faecalis and Escherichia coli.

The compounds according to the invention are particularly active against typical and atypical mycobacteria and Helicobacter pylori and also against bacteria-like microorganisms, such as, for example, mycoplasma and rickettsia. They are therefore particularly highly suited in human and veterinary medicine for the prophylaxis and chemotherapy of local and systemic infections which are caused by these pathogens.

The compounds are furthermore particularly highly suited for the control of protozoonoses and helminthoses.

The compounds according to the invention can be used in various pharmaceutical preparations. Preferred pharmaceutical preparations which may be mentioned are tablets, mated tablets, capsules, pills, granules, suppositories, solutions, suspensions and emulsions, pastes, ointments, gels, creams, lotions, powders and sprays.

The compounds according to the invention can also be linked with [Mactam derivatives such as, for example, cephalosporins or peneros via covalent bonds to give so-called dual-action derivatives.

In the following Tables 9 and 10, the minimum inhibitory concentration are shown as a measure of the antibacterial activity and the ID50 values as a measure of the interactions with mammalian DNA of a substance both for compounds according to the invention and for reference compounds from the prior art (EP 520 240). These data confirm that, combined with high antibacterial activity, the compounds according to the invention have significantly fewer interactions with mammalian DNA.

The minimum inhibitory concentration (MIC) were determined by a serial dilution method on Iso-Sensitest Agar (Oxoid). For each test substance, a number of agar plates were prepared which, with doubled dilution in each case, contained decreasing concentrations of the active compound. The agar plates were inoculated using a multipoint inoculator (Denley). For inoculation, overnight cultures of the pathogens were used which had previously been diluted such that each inoculation point contained about 104 colony-forming particles. The inoculated agar plates were incubated at 37° C. and the microorganism growth was read off after about 20 hours. The MIC value (μg/ml) indicates the lowest active compound concentration at which no growth could be detected using the naked eye.

$ID_{50}$ is understood as meaning the concentration of a substance at which the DNA synthesis in cells from ovaries of the Chinese hamster (CHO-KI) is inhibited by 50%. This value is determined over defined time intervals in decreasing dilution steps after incubation of the appropriate substances. To do this, the DNA synthesis in CHO-KI cells is determined in comparison to controls by means of fluorophotometric methods.

TABLE 9

MIC values (μg/ml) and ID$_{50}$ values of active compounds according to the invention

| | | Example | | | | |
|---|---|---|---|---|---|---|
| Species | Strain | 2 | 3 | 4 | 8 | 9 |
| E. coli | Neumann | ≤0.015 | ≤0.015 | ≤0.015 | ≤0.015 | ≤0.015 |
| Staph. aureus | 133 | 0.06 | ≤0.015 | ≤0.015 | 0.03 | 0.06 |
| Staph. aureus | ICB 25701 | 2 | 0.25 | 0.5 | 0.5 | 8 |
| Ps. aeruginosa | Walter | 1 | 0.5 | 0.5 | 0.5 | 1 |
| Bac. fragilis | ES 25 | 1 | 0.125 | 2 | 0.5 | 4 |
| ID$_{50}$ (μg/ml) | | 32 | 32 | >64 | 16 | 32 |

TABLE 10

MIC values (μg/ml) and ID$_{50}$ values of active compounds from the prior art

| | | Examples from EP 520 240 | | |
|---|---|---|---|---|
| | | 35 | | 36 |
| Species | Strain | Ref. 1 | Ref. 2 | Ref. 3 |
| E. coli | Neumann | 0.015 | 0.015 | 0.015 |
| Staph. aureus | 133 | 0.015 | 0.015 | 0.015 |
| Staph. aureus | ICB 25701 | 0.06 | 0.015 | 0.015 |
| Ps. aeruginosa | Walter | 0.5 | 1 | 0.5 |
| Bac. fragilis | ES 25 | 0.5 | 0.25 | 0.125 |
| ID$_{50}$ (μg/ml) | | 0.015 | 0.1 | 0.1 |

Ref. 1: 7-(4-Amino-7-methyl-1,3,3a,4,7,7a-hexahydro-isoindol-2-yl)-1-cyclopropyl-6,8-difluoro-1,4-dihydro-4-oxo-3-quinolinecarboxylic acid,
Ref. 2: 7-(4-Amino-7-methyl-1,3,3a,4,7,7a-hexahydro-isoindol-2-yl)-1-cyclopropyl-6-fluoro-1,4-dihydro-8-methoxy-4-oxo-3-quinolinecarboxylic acid,
Ref. 3: 7-(4-Amino-7-methyl-1,3,3a,4,7,7a-hexahydro-isoindol-2-yl)-8-chloro-1-cyclopropyl-6-fluoro-1,4-dihydro-4-oxo-3-quinolinecarboxylic acid.

Preparation of the intermediates

EXAMPLE Z 1

A. Ethyl 8-benzyl-8-azabicyclo[4.3.0]non-3-ene-1-carboxylate (ethyl 2-benzyl-1,2,3,4,7,7a-hexahydro-isoindole-3a-carboxylate)

231 g (1 mol) of ethyl 1-benzyl-2,5-dihydropyrrole-3-carboxylate and 10 g of 4-tert-butylpyrocatechol are dissolved in 1500 ml of toluene, 20 bar of nitrogen are injected and 350 g of 1,3-betadiene are then blown into the autoclave. The mixture is heated at 120° C. for three days and cooled, the pressure is released, and the solution is concentrated and distilled. Yield: 264.9 g (87.6% of theory), boiling point: 127°–140° C./0.1 mbar. The product is 94% pure according to gas-chromatographic detemination.

B. 1-Ethyl8-methyl 8-azabicyclo[4.3.0]non-3-ene-1,8-dicarboxylate (3a-ethyl 2-methyl 1,2,3,4,7,7a-hexahydro-isoindole-2,3a-dicarboxylate)

16.4 g (57.5 mmol) of 94% pure ethyl 8-benzyl-8-azabicyclo [4.3.0]non-3-ene-1-carboxylate are dissolved in 130 ml of absolute chlomforn, 7.5 g of Na$_2$CO$_3$ are added and 12 g (0.12 mol) of methyl chloroformate are then added dropwise. The mixture is heated under reflux overnight, the salts are filtered off with suction, the fillrate is concentrated and the residue is distilleck Yield: 14.4 g (90% of theory), boiling point: 122°–126° C./0.2 mbar. The product is 91% pure according to gas-chromatographlc determination.

C. 1-Ethyl 8-methyl 8-azabicyclo[4.3.0]nona-2,4-diene-1,8-dicarboxylate (3a-ethyl 2-methyl 1,2,3,7a-tetrahydro-isoindole-2,3a-dicarboxylate)

30 g (0.187 mol) of bromine are added dropwise while cooling using a water bath to 46 g (0.17 mol) of 94% pure 1-ethyl 8-methyl 8-azabicyclo[4.3.0]non- 3-ene-1,8-dicarboxylate in 200 ml of absolute chloroform and the mixture is stirred at room temperature for two hours. It is concentrated, the residue is taken up in 1l of absolute toluene and 61 g (0.4 mol) of 1,8-diazabicyclo[5.4.0] undec-7-ene are addeeL The mixture is heated under reflux for three hours, decanted from the deposited crystals alter cooling and the solution is washed with water, dried over MgSO4, concentrated and distilled. Yield: 22.3 g (50% of theory), boiling point: 125°–135° C./0.15 mbar. The product is 95.5% pure by gas chromatography.

D. 8-Azabicyelo[4.3.0]nona-2,4-diene-1.8-dicarboxylic acid 8-methyl ester (1.2,3,7a-tetrahydro-isoindole-2, 3a-dicarboxylie acid 2-methyl ester)

1. 22 g(83.6 mmol)of 95.5% pure 1-ethyl 8-methyl 8-azabicyclo[4.3.0]nona-2,4-diene-1,8-dicarboxylate ester are heated under reflux overnight with 3.7 g (92.5 mmol) of NaOH in 60 ml of methanol. The solution is concentrated, the residue is taken up in 40 ml of water and the solution is extracted once with tert-butyl methyl ether. The aqueous solution is rendered acidic ming 8 ml of concentrated hydrochloric acid and extracted several times with methylene chloride. After drying over MgSO$_4$, it is concentrated. Yield: 20.9 g as an oil.

2. 32 g (0.76 mol) of LiOH.H$_2$O in 300 ml of water are added dropwise at room temperature to 170 g (0.61 mol, 90% pure by gas chromatography) of 1-ethyl 8-methyl 8-azabicyclo[4.3.0]nona-2,4-diene-1,8-dicarboxylate in 300 ml of tetrahydrofuran and the mixture is stirred overnight at room temperature. The tetrahydrofuran is distilled off, the aqueous solution is extracted once with tert-butyl methyl ether, then rendered acidic using concentrated hydrochloric acid and extracted several times with CH$_2$Cl$_2$. The organic solutions are dried over MgSO$_4$ and concentrated, and the crystallizing product is recrystallized from toluene. Yield: 115 g (84.5% of theory), melting point: 107°–110° C.

E. Methyl 1-methoxycarbonylamino-8-azabicyclo[4.3.0] nona-2,4-diene-8-carboxylate (methyl 3a-methoxyearbonylamino-1,2,3,7a-tetrahydro-isoindole-2-carboxylate)

20.9 g of crude 8-azabicyclo[4.3.0]nona-2,4-diene-1,8-dicarboxylic acid 8-methyl ester are heated under reflux overnight with 9.6 g (92 mmol) of triethylamine, 26 g (107 mmol) of diphenylphosphoryl azide and 5 g of methanol in 300 ml of absolute toluene. The solution is washed with water, dried over MgSO$_4$, and concentrated. The product is processed further in crude form. Yield: 20 g.

F. 1,2,3,7a-Tetrahydro-isoindol-3a-ylamine (1-amino-8-azabicyclo[4.3.0]nona-2,4-diene)

20 g of crude methyl 1-methoxycarbonylamino-8-azabicyclo[4.3.0]nona-2,4-diene-8-carboxylate are heated with 75 g (0.235 mol) of Ba(OH)$_2$.8 H$_2$O in 250 ml of water overnight under reflux. The BaCO$_3$ is filtered off with suction, the filtrate is concentrated and the salt residues are boiled three times with 1,4-dioxane. The dioxane solutions are concentrated and the residue is distilled. Yield: 5 g (43.9% of theory based on Step D), boiling point: 65° C./0.2 mbar.

G. (1S,6S)-8-Azabicyclo[4.3.0]nona-2,4-diene-1,8-dicarboxylic acid 8-methyl ester (3aS,7aS)-1,2,3,7a-tetahydro-isoindole-2,3a-dicarboxylic acid 2-methyl ester)

Resolution method 1: 100 g (0.448 mol) of 8-azabicyclo[4.3.0]nona-2,4-diene-1,8-dicarboxylic acid 8-methyl ester are dissolved in a mixture of 750 ml of diisopropyl ether and 750 ml of tetrahydrofuran and 27 g (0.223 mol) of R-(+)-1-phenylethylamine are added. The mixture is stirred overnight at room temperature, and the crystals are filtered off with suction, washed with cold tetrahydrofuran and dried in air. Yield: 57 g of salt, $[\alpha]_D$=+156° (c=1.2, methanol), The crystals are recrystallized from 600 ml of isopropanol. Yield: 41 g (53.4% of theory), $[\alpha]_D$=+197° (c=1.1, methanol).

Resolution method 2: 199 g (0.892 mol) of 8-azabicyclo[4.3.0]nona-2,4-diene-1,8-dicarboxylic acid 8-methylester are dissolved in an mixture of 800 ml of diisopropyl ether and 600 ml of tetrahydrofuran and 54 g (0.446 mol) of S-(−)-1-phenylethylamine are added. The mixture is stirred overnight at room temperature. The crystals are filtered off with suction, and the isolated salt is recrystallized from 1 l of isopropanol. Yield: 65.5 g (42.6% of theory), $[\alpha]_D$: −205.4° (c=0.97, methanol).

The combined mother liquors are concentrated, and the residue is dissolved in 1 l of tert.-butyl methyl ether. The solution is extracted with a mixture of 30 g of concentrated sulfuric acid and 200 ml of icewater, and the aqueous layer is reextracted with tert.-butyl methyl ether. The combined tert.-butyl methyl ether solutions are dried over $MgSO_4$ and concentrated. Yield: 170.4 g.

This enantiomerically enriched (+)-8-azabicyclo[4.3.0]nona-2,4-diene-1,8-dicarboxylic acid 8-methylester is dissolved in a mixture of 800 ml of diisopropyl ether and 600 ml of tetrahydrofuran, and 55 g of R-(+)-1-phenylethylamine are added. The salt is filtered off with suction, washed with tetrahydrofuran/diisopropyl ether and dried in air. Yield: 141 g (91.8% of theory), $[\alpha]_D$: +161.1° (c=0.928, methanol).

The salt is recrystallized twice from isopropanol/diisopropyl ether (4:1). Yield: 112.5 g, $[\alpha]_D$: +215.7° (c=1.1, methanol). Liberation of the acid: 17 g (49.3 mmol) of these crystals are suspended in 100 ml of ice-water and the mixture is acidified with 3 ml of concentrated sulphuric acid. It is then extracted three times using 100 ml of tert-butyl methyl ether each time, and the organic phases are dried over $MgSO_4$ and concentrated. Crude yield: 13.2 g, melting point: 79°–81° (from diisopropyl ether), $[\alpha]_D$=+254° (c=0.85, $CH_2Cl_2$)

H. Methyl (1S,6R)-1-methoxycarbonylamino-8-azabicyclo [4.3.0]nona-2,4-diene-8-carboxylate (methyl (3aS,7aR)-3a-methoxycarbonylamino-1,2,3,7a-tetrahydro-isoindole-2-carboxylate)

Analogously to Step E, 13 g of crude (1S,6S)-8-azabicyclo[4.3.0]nona-2,4-diene-1,8-dicarboxylic acid 8-methyl ester are reacted with 5 g (50 mmol) of tdethylamine, 3.2 g of methanol and 13.7 g (55 mmol) of diphenylphosphoryl azide in 160 ml of absolute toluene and worked up accordingly. Crude yield: 11.2 g I. (3aS,7aR)-1,2,3,7a-Tetrahydro-isoindol-3a-ylamine ((1S,6R)-1-amine-8-azabicyclo[4.3.0]nona-2,4-diene)

Analogously to Step F, 11 g of crude methyl (1S,6R)-1-methoxycarbonylamino-8-azabicyclo[4.3.0]nona-2,4-diene-8-carboxylate are hydrolysed in 150 ml of water using 42 g of Ba(OH)$_2$.8 H$_2$O and worked up accordingly. Yield: 3 g (44.6% of theory based on Step G), boiling point: 70° C./0.1 mbar, $[\alpha]_D$=+235.9° (c=1,14, methanol).

J. (1R,6R)-8-Azabicyclo[4.3.0]nona-2,4-diene-1,8-dicarboxylic acid 8-methyl ester ((3aR,7aR)-1,2,3,7a-tetrahydro-isoindole-2,3a-dicarboxylic acid 2-methyl ester)

Analogously to Step G (method 1), resolution of the racemate is carded out using S-(−)-phenylethylamine and (1R,6R)-8-azabicyclo[4.3.0]nona-2,4-diene-1,8-dicarboxylic acid 8-methyl ester is obtained, $[\alpha]_D$=−233.6° (c=0.6, $CH_2Cl_2$).

K. Methyl (1R,6S)-1-methoxycarbonylamino-8-azabicyclo[4.3.0]nona-2,4-diene-8-carboxylate (methyl(3aR,7aS)-3a-methoxycarbonylamino-1,2,3,7a-tetrahydro-isoindole-2-carboxylate)

The product from Step J is reacted analogously to Step H and methyl (1R,6S)-1-methoxycarbonylamino-8-azabicyclo[4.3.0]nona-2,4-diene-8-carboxylate is obtained, which is reacted further as a crude product.

L. (3aR,7aS)-1,2,3,7a-Tetrahydro-isoindol-3a-ylamine ((1R,6S)-1-amino-8-azabicyclo[4.3.0]nona-2,4-diene)

The product obtained in Step K is reacted analogously to the details in Step F, $[\alpha]_D$: −224° (c=0.8, methanol).

M. Methyl 8-azabicyclo[4.3.0]nona-2,4-diene-1-carboxamide-8-carboxylate (methyl 1,2.3.7a-tetrahydro-isoindole-3a-carboxamide-2-carboxylate)

4.5 g (20 mmol) of 8-azabicyclo[4.3.0]nona-2,4-diene-1,8-dicarboxylic acid 8-methyl ester are initially introduced into 20 ml of absolute $CH_2Cl_2$ and 2.2 g (22 mmol) of triethylamine are added. The mixture is cooled to −20° C., 2.6 g (25 mmol) of ethyl chloroformate are added dropwise and it is stirred at −20° C. for one hour. 20 ml of 25% strength aqueous ammonia solution are then added dropwise at this temperature, and the mixture is allowed to come to room temperature and is stirred for a further 1 hour. It is then extracted several times with $CH_2Cl_2$, and the extracts are dried over $MgSO_4$ and concentrated. The product crystallizes. Yield: 4.4 g (99% of theory), melting point: 117°–120° C. (from toluene).

N. Methyl 1-amino-8-azabicyclo[4.3.0]nona-2,4-diene-8-carboxylate (methyl 3a-amino-1,2,3,7a-tetrahydro-isoindole-2-carboxylate)

4.3 g (19.4 mmol) of methyl 8-azabicyclo [4.3.0]nona-2,4-diene-1-carboxamide-8-carboxylate are heated with 7.9 g (20.2 mmol) of I-hydroxy-I-tosyloxyiodobenzene in 100 ml of absolute acetonitrile for 3 hours under reflux. The solution is concentrated, the residue is taken up in 100 ml of $CHCl_3$, the solution is washed with 15% strength KOH solution, dried over $MgSO_4$ and concentrated, and the residue is distilled in a high vacuum. Yield: 1.5 g (40% of theory), boiling point: 122°–125° C./0.07 mbar.

O. 1,2,3,7a-Tetrahydro-isoindol-3a-ylamine (1-amino-8-azabicyclo[4.3.0]nona-2,4-diene)

Analogously to Step F, 1.4 g (7.2 mmol) of methyl 1-amino-8-azabicyclo[4.3.0]nona-2,4-diene-8-carboxylate are hydrolysed using 4 g of Ba(OH)$_2$.8H$_2$O in 20 ml of water and worked up accordingly. Yield: 0.6 g (61% of theory), boiling point: 65° C./0.1 mbar.

Preparation of the active compounds

EXAMPLE 1

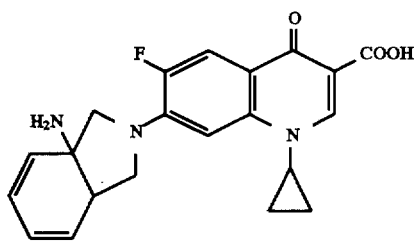

265 mg (1 mmol) of 1-cyclopropyl-6,7-difluoro-1,4-dihydro-4-oxd-3-quinolinecarboxylic acid are heated under reflux for 1 hour in a mixture of 4 ml of acetonitrile and 2 ml of dirnethylformamide with 170 mg (1.5 mmol) of 1,4-diazabicyclo[2.2.2]octane and 150 mg (1.1 mmol) of 1,2,3,7a-tetrahydro-isoindol-3a-ylamine. The precipitate which is deposited is filtered off with suction, washed with 30 ml of water and dried.

Yield: 288 mg (75.6% of theory) of 7-(3a-amino-1,2,3,7a-tetrahydro-isoindol-2-yl)-1-cyclopropyl-6-fluoro-1,4-dihydro-4-oxo-3-quinolinecarboxylic acid, melting point: 272°–274° C. (with decomposition).

EXAMPLE 2

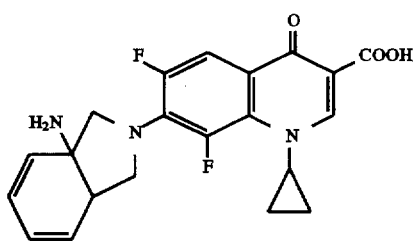

Under corresponding conditions to those in Example 1, using 1-cyclopropyl-6,7,8-trifluoro- 1,4-dihydro-4-oxo-3-quinolinecarboxylic acid 7-(3a-amino-1,2,3,7a-tetrahydroisoindol-2-yl)-1-cyclopropyl-6,8-difluoro-1,4-dihydro-4-oxo-3-quinolinecarboxylic acid of melting point: 232°–233° C. (with decomposition) is obtained in 85% yield.

EXAMPLE 3

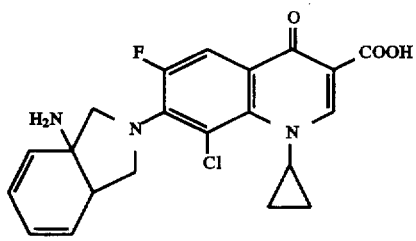

Under corresponding conditions to those in Example 1, using 8-chloro-1-cyclopropyl-6,7-difluoro-1,4-dihydro-4-oxo-3-quinolinecarboxylic acid 7-(3a-amino-1,2,3,7a-tetrahydro-isoindol-2-yl)-8-chloro-1-cyclopropyl-6-fluoro-1,4-dihydro-4-oxo-3-quinolineearboxylic acid of melting point: 179°–182° C. (with decomposition) is obtained in 58% yield.

EXAMPLE 4

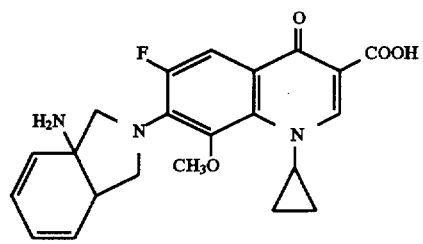

295 mg (1 mmol) of 1-cyclopropyl-6,7 -difluoro-1,4-dihydro-8-methoxy-4-oxo-3-quinolineearboxylic acid are heated under reflux for 1 hour with 330 mg (2.4 mmol) of 1,2,3,7a-tetrahydro-isoindol-3a-ylamine in a mixture of 4 ml of acetonitrile and 2 ml of dimethylformamide. The mixture is concentrated, the residue is stirred with 40 ml of water, and the precipitate which is slowly deposited is filtered off with suction, washed with water and dried at 60° C in a high vacuum.

Yield: 175 mg (43% of theory of 7-(3a-amino-1,2,3,7a-tetrahydro-isoindolo2-yl)-1-cyclopropyl-6-fluoro-1,4-dihydro-8-methoxy-4-oxo-3-quinolinecarboxylic acid, melting point: 195°–196° C. (with decomposition).

EXAMPLE 5

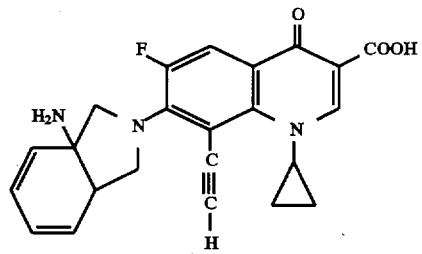

289 mg (1 mmol) of 1-cyclopropyl-8-ethinyl-6,7-difluoro-1,4-dihydro-4-oxo-3-quinolinecarboxylic acid are heated under reflux for 1 hour with 170 mg (1.5 mmol) of 1,4-diazabicyclo[2.2.2]octane and 150 mg (1.1 mmol) of 1,2,3,7a-tetrahydro-isoindol-3a-ylamine in a mixture of 4 ml of acetonitrile and 2 ml of dimethylforrnamide. The mixture is concentrated, the residue is stirred with water (pH=8) and adjusted to pH=7 with dilute hydrochloric acid, and the precipitate which is deposited is filtered off with suction, washed with water and dried.

Yield: 382 mg (94% of theory) of 7-(3a-amino-1,2,3,7a-tetrahydro-isoindol-2-yl)-1-cyclopropyl-8-ethinyl-6-fluord-1,4-dihydro-4-oxo-3-quinolinecarboxylic acid, melting point: 176°–177° C. (with decomposition).

EXAMPLE 6

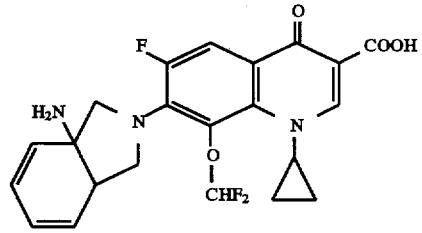

Under corresponding conditions to those in Example 5, using 1-cyclopropyl-8-difluoromethoxy-6,7-difluoro-1,4- dihydro-4-oxo-3-quinolinecarboxylic acid 7-(3a-amino-1,2,3,7a-tetrahydro-isoindol-2-yl)-1-cyclopropyl-8-difluoromethoxy-6-fluoro-1,4-dihydro-4-oxo-3-quinolinecarboxylic acid of melting point: 215°–217° C. (with decomposition) is obtained in 66% yield.

EXAMPLE 7

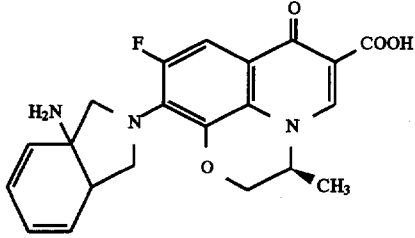

Under corresponding conditions to those in Example 1, using (S)-9,10-difluoro-2,3-dihydro-3-methyl-7-oxo-7H-pyrido[1,2,3-d,e][1,4]benzoxazine-6-carboxylicacid10-(3-amino-1,2,3,7a-tetrahydro-isoindol-2-yl)-9-fluoro-2,3-dihydro-3(S)-methyl-7-oxo-7H-pyrido[1,2,3-d,e][1,4]benzoxazine-6-carboxylic acid of melting point: 242°–243° C. (with decomposition) is obtained in 45% yield.

EXAMPLE 8

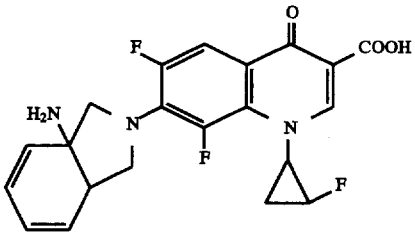

Under corresponding conditions to those in Example 1, using racemic 6,7,8-trifluoro-1-(cis-2-fluorocyclopropyl)-1,4-dihydro-4-oxo-3-quinolinecarboxylic acid 7-(3a-amino-1,2,3,7a-tetrahydro-isoindol-2-yl)-6,8-difluoro-1-(cis-2-fluorocyclopropyl)-1,4-dihydro-4-oxo-3-quinolinecarboxylic acid of melting point: 210°–211° C. (with decomposition) is obtained in 66% yield.

EXAMPLE 9

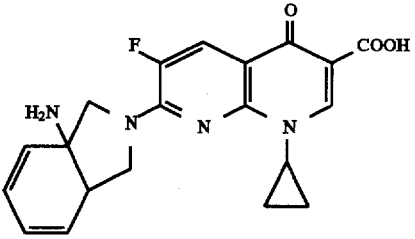

283 mg (1 mmol) of 7-chloro-1-cyclopropyl-6-fluoro-1,4-dihydro-4-oxo-1,8-naphthyridine-3-carboxylic acid are treated with 270 mg (2 mmol) of 1,2,3,7a-tetrahydro-isoindol-3a-ylamine in 6 ml of acetonitrile at 25° C. and the mixture is stirred at 50° C. for 1 hour. The suspension is cooled in an ice bath, and the precipitate is filtered off with suction, washed with acetonitrile and stirred with water, and dried at 80° C./0.1 mbar.
Yield: 262 mg (67% of theory) of 7-(3a-amino-1,2,3,7a-tetrahydro-isoindol-2-yl)-1-cyclopropyl-6-fluoro-1,4-dihydro-4-oxo-1,8-naphthyridine-3-carboxylic acid, melting point: 239°–240° C. (with decomposition).

EXAMPLE 10

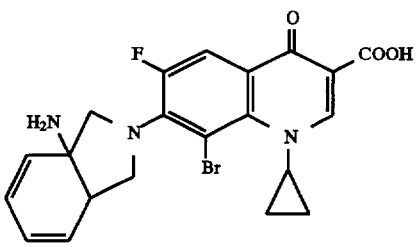

Under corresponding conditions to those in Example 1, using 8-bromo-1-cyclopropyl-6,7-difluoro-1,4-dihydro-4-oxo-3-quinolinecarboxylic acid a reaction mixture from which 7-(3a-amino-1,2,3,7a-tetrahydro-isoindol-2-yl)-8-bromo-1-cyclopropyl-6-fluoro-1,4-dihydro-4-oxo-3-quinolinecarboxylic acid was isolated by chromatography on silica gel (eluent: dichloromethane/methanol/17% ammonia=30:8:1) is obtained; melting point: 200°–201° C. (with decomposition).

EXAMPLE 11

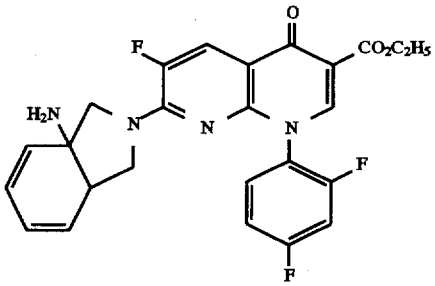

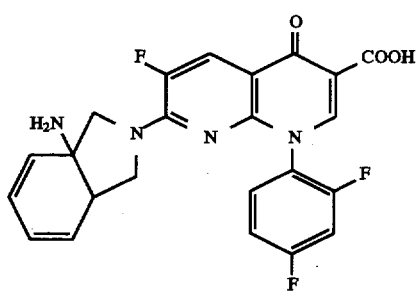

A. 358 mg (1 mmol) of ethyl 7-chloro-1-(2,4-difluorophenyl)-6-fluoro-1,4-dihydro-4-oxo-1,8-naphthyridine-3-carboxylate are treated with 202 mg (1.5 mmol) of 1,2,3,7a-tetrahydro-isoindol-3a-ylamine in 6 ml of acetonitrile and the mixture is stirred at 30° C. for 2 hours. The precipitate is filtered off with suction, washed with acetonitrile, dried at 90° C./0.1 mbar (crude yield: 255 mg) and purified by chromatography on 15 g of silica gel (eluent:dichloromethane/methanol/17% ammonia 30:8:1).
Yield: 86 mg (18% of theory) of ethyl 7-(3a-amino-1,2,3,7a-tetrahydro-isoindol-2-yl)-6-fluoro-1-(2,4-difluorophenyl)-1,4-dihydro-4-oxo-1,8-naphthyridine-3-carboxylate, Melting point: 202°–207° C. (with decomposition).

B. 80 mg of the product from Step A are heated under reflux for 2 hours in a mixture of 1 ml of acetic acid and 0.75 ml of half-concentrated hydrochloric acid. The mixture is concentrated, the residue is stirred with a little water, and the precipitate is filtered off with suction, washed with water and dried at 100° C. in a high vacuum.

Yield: 37 mg (45% of theory) of 7-(3a-amino-1,2,3,7a-tetrahydro-isoindol-2-yl)-6-fluoro-1-(2,4-difluorophenyl)-1,4-dihydro-4-oxo-1,8-naphthyridine-3-carboxylic acid hydrochloride, melting point: 208°–210° C. (with decomposition).

EXAMPLE 12

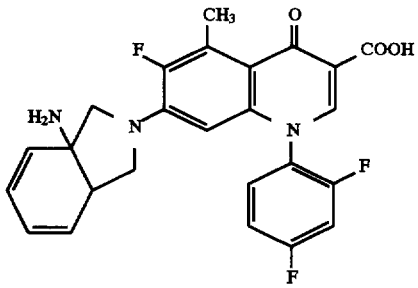

Under corresponding conditions to those in Example 4, using 1-(2,4-difluorophenyl)-6,7-difluoro-1,4-dihydro-5-methyl-4-oxo-3-quinolinecarboxylic acid 7-(3a-amino- 1,2,3,7a-tetrahydro4soindol-2-yl)-1-(2,4-difluorophenyl)-6-fluoro-1,4-dihydro-5-methyl-4-oxo-3-quinolinecarboxylic acid is obtained in 89% yield, melting point: 157°–159° C. (with decomposition).

EXAMPLE 13

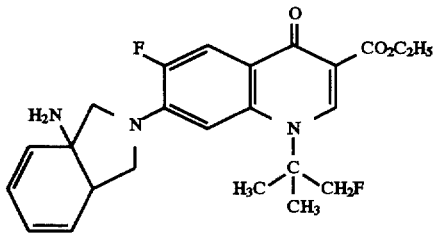

Under corresponding conditions to those in Example 1, using ethyl 6,7-difluoro-1-(fluoro-tert-butyl)-1,4-dihydro-4-oxo-3-quinolinecarboxylic acid a reaction mixture from which ethyl 7-(3a-amino-1,2,3,7a-tetrahydro-isoindol-2-yl)-6-fluoro-1-(fluoro-tert-butyl)-1,4-dihydro-4-oxo-3-quinolinecarboxylic acid was isolated by chromatography on silica gel (dichloromethane/methanol=95:5) is obtained, melting point: 219°–220° C. (with decomposition).

EXAMPLE 14

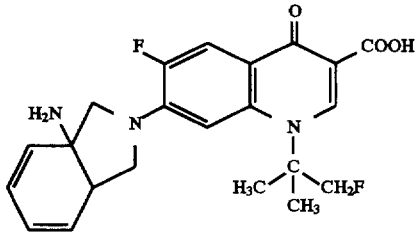

Under corresponding conditions to those in Example 4, using 6,7-difluoro-1-(fluoro-tert-butyl)-1,4-dihydro-4-oxo-3-quinolinecarboxylic acid 7-(3a-amino-1,2,3,7a-tetrahydro-isoindol-2-yl)-6-fluoro-1-(fluoro-tert-butyl)-1,4-dihydro-4-oxo-3-quinolinecarboxylic acid of melting point: 229°–231° C. (with decomposition) is obtained in 78% yield.

EXAMPLE 15

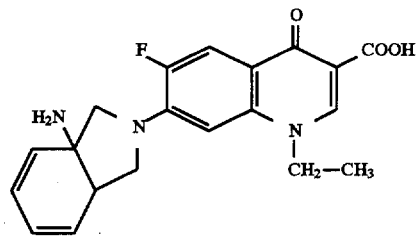

Under corresponding conditions to those in Example 1, using 1-ethyl-6,7-difluoro-1,4-dihydro-4-oxo-3-quinolinecarboxylic acid 7-(3a-amino-1,2,3,7a-tetrahydro-isoindol-2-yl)-1-ethyl-6-fluoro-1,4-dihydro-4-oxo-3-quinolinecarboxylic acid of melting point: 229° C. (with decomposition) is obtained in 63% yield.

EXAMPLE 16

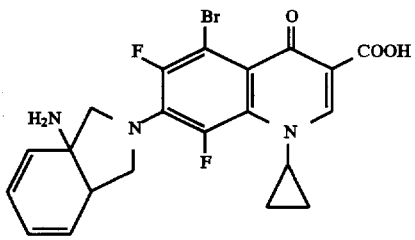

Under corresponding conditions to those in Example 1, using 5-bromo-1-cyclopropyl-6,7,8-trifluoro-1,4-dihydro-4-oxo-3-quinolineearboxylic acid 7-(3a-amino-1,2,3,7a-tetrahydro-isoindol-2-yl)-5-bromo-1-cyclopropyl-6,8-difluoro-1,4-dihydro-4-oxo-quinolinecarboxylic acid of melting point: 278°–280° C. (with decomposition) is obtained in 71% yield.

EXAMPLE 17

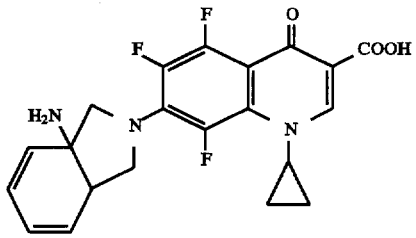

Under corresponding conditions to those in Example 1, using 1-cyclopropyl-5,6,7,8-tetrafluoro-1,4-dihydro-4-oxo-3-quinolinecarboxylic acid 7-.(3a-amino-1,2,3,7a-tetrahydro-isoindol-2-yl)-1-cyclopropyl-5,6,8 -trifluoro-1,4-dihydro-4-oxo-3-quinolinecarboxylic acid is obtained in 70% yield, melting point: 244°–245° C. (with decomposition).

EXAMPLE 18

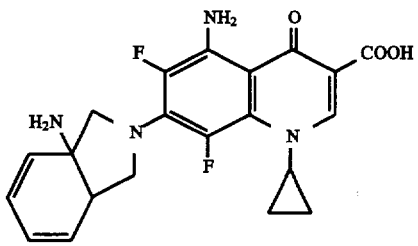

A stream of ammonia is passe,d into a solution of 50 mg (0.12 mmol) of 7-(3a-amino-1,2,3,7a-tetrahydro-isoindol-2-yl)-1-cyclopropyl-5,6,8-trifluoro-1,4-dihydro-4-oxo-3-quinolinecarboxylic acid in 5 ml of dimethyl sulphoxide at 110° C. to 120° C. for 14 hours. The mixture is evaporated and the residue is stirred with 8 ml of ethanol. The undissolved precipitate is filtered off with suction, washed with ethanol, dried at 60° C. in a high vacuum (27 mg of crude product) and purified by chromatography (silica gel, eluent:dichloromethane/methanol=95:5).

Yield: 18 mg of 5-amino-7-(3a-amino-1,2,3,7a-tetrahydro-isoindol-2-yl)-1-cyclopropyl- 6,8-difluoro-1,4-dihydro-4-oxo-3-quinolidecarboxylic acid, melting point: 194°–195° C. (with decomposition).

EXAMPLE 19

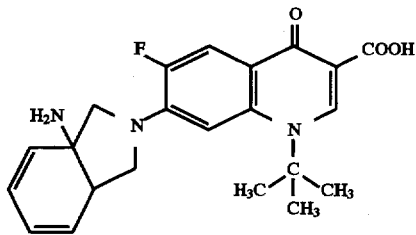

Under corresponding conditions to those in Example 5, using 1-tert-butyl-6,7-difluoro-1,4-dihydro-4-oxo-3-quinolinecarboxylic acid 7-(3a-amino-1,2,3,7a-tetrahydro-isoindol-2-yl)-1-tert-butyl-6-fluoro-1,4-dihydro-4-oxo-3-quinolinecarboxylic acid of melting point: 228°–230° C. (with decomposition) is obtained in 69% yield.

EXAMPLE 20

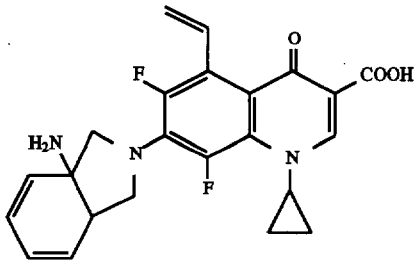

Under corresponding conditions to those in Example 4, using 1-cyclopropyl-6,7,8-trifluoro-1,4-dihydro-4-oxo-5-vinyl-3-quinolinecarboxylic acid 7-(3a-amino-1,2,3,7a-tetrahydro-isoindol-2-yl)-1-cyclopropyl-6-fluoro-1,4-dihydro-4-oxo-5-vinyl-3-quinolinecarboxylic acid is obtained in 75% yield, melting point: 227°–228° C. (with decomposition).

EXAMPLE 21

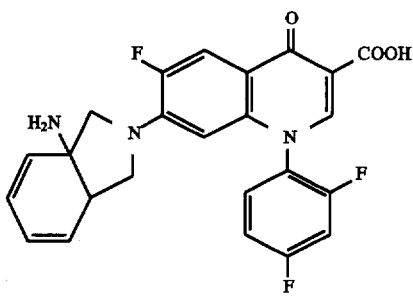

Under corresponding conditions to those in Example 4, using 1-(2,4-difluorophenyl)-6,7-difluoro-1,4-dihydro-4-oxo-3-quinolinecarboxylic acid 7-(3a-amino-1,2,3,7a-tetrahydro-isoindol-2-yl)-1-(2,4-difluorophenyl)-6-fluoro-1,4-dihydro-4-oxo-3-quinolinecarboxylic acid of melting point: 253°–254° C. (with decomposition) is obtained in 77% yield.

EXAMPLE 22

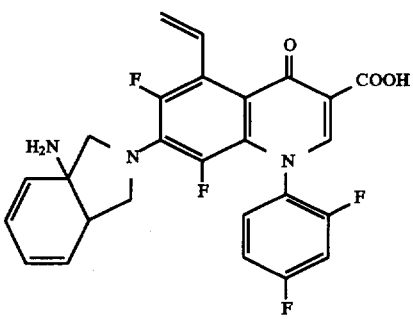

Under corresponding conditions to those in Example 4, using 1-(2,4-difluorophenyl)-6,7,8-trifluoro-1,4-dihydro-4-oxo-5-vinyl-3-quinolinecarboxylic acid 7-(3a-amino-1,2,3,7a-tetrahydro-isoindol-2-yl)-1-(2,4-difluorophenyl)-6,8-difluoro-1,4-dihydro-4-oxo-5-vinyl-3-quinolinecarboxylic acid of melting point: 215°–216° C. (with decomposition) is obtained in 96% yield.

EXAMPLE 23

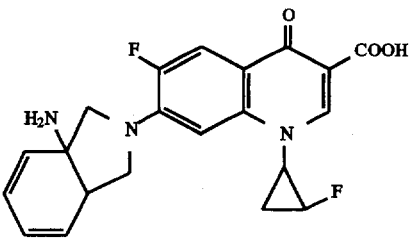

Under corresponding conditions to those in Example 1, using racemic 6,7-difluoro-1-(cis-2-fluorocyclopropyl)-1,4-dihydro-4-oxo-3-quinolinecarboxylic acid 7-(3a-amino-1,2,3,7a-tetrahydro-isoindol-2-yl)-6-fluoro-1-(cis-2-fluorocyclopropyl)-1,4-dihydro-4-oxo-3-quinolinecarboxylic acid of melting point: 238°–239° C. (with decomposition) is obtained in 55% yield.

EXAMPLE 24

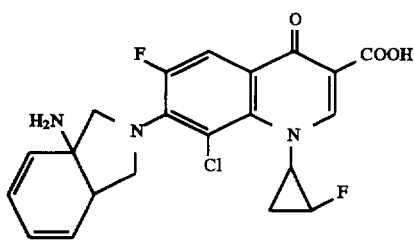

Under corresponding conditions to those in Example 1, using racemic 8-chloro-6,7-difluoro-1-(cis-2-fluorocydopropyl)-1,4-dihydro-4-oxo-3-quinolinecarboxylic acid 7-(3a-amino-1,2,3,7a-tetrahydro-isoindol-2-yl)-8-chloro-6-fluoro-1-(cis-2-fluorocyclopropyl)-1,4-dihydro-4-oxo-3-quinolinecarboxylic acid of melting point: 196°–198° C. (with decomposition) (after chromatographic purification with dichloromethane/methanol (95:5) on silica gel) is obtained in 52% yield.

EXAMPLE 25

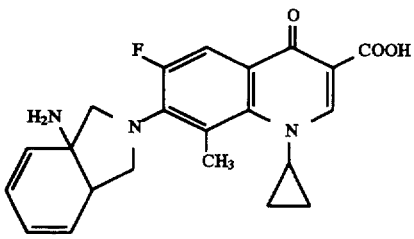

410 mg (1 mmol) of 1-cyclopropyl-6,7-difluoro-1,4-dihydro-8-methyl-4-oxo-3-quinolinecarboxylic acid B(O-CO-CH$_3$)$_2$-chelate are heated at 60°–70° C. for 15 hours with 224 mg (2 mmol) of 1,4-diazabicyclo[2.2.2]octane and 272 mg (2 mmol) of 1,2,3,7a-tetrahydro-isoindol-3a-ylamine under nitrogen in 8 ml of acetonitrile. The mixture is concentrated in vacuo and a mixture of 4 ml of acetone and 0.5 ml of concentrated hydrochloric acid is added to the residue and the mixture is treated in an ultrasonic bath for 30 minutes. It is concentrated, the residue is taken up in water (pH 3), the precipitated 1-cyclopropyl-6,7-difluoro-1,4-dihydro-8-methyl-4-oxo-3-quinolinecarboxylic acid (90 mg) is filtered off with suction and the mother liquor is adjusted to pH 7.5 using 5% strength sodium bicarbonate solution. The mixture is extracted with dichloromethane, dried with sodium sulphate and concentrated.

Yield: 61 mg (15% of theory) of 7-(3a-amino-1,2,3,7a-tetrahydro-isoindol-2-yl)-1-cyclopropyl-6-fluoro-1,4-dihydro-8-methyl-4-oxo-3-quinolinecarboxylic acid, melting point: 201°–203° C. (with decomposition).

EXAMPLE 26

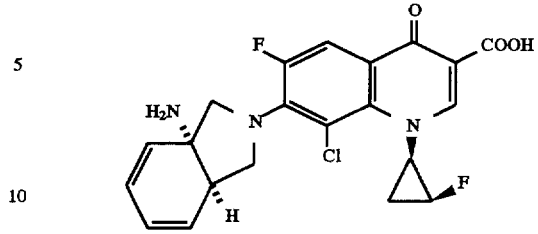

317 mg(1 mmol) of 8-chloro-6,7-difluoro-1-[(1R,2S)-2-fluorocyclopropyl]-1,4-dihydro-4-oxo-3-quinolinecarboxylic acid are heated under reflux for 1 hour with 187 mg (1.67 mmol) of 1,4-diazabicyclo[2.2.2]octane and 165 mg (1.2 mmol) of (3aS,7aR)- 1,2,3,7a-tetrahydro-isoindol-3a-ylamine in a mixture of 4 ml of acetonitrile and 2 ml of dimethylformamide. The solution remains standing overnight in a refrigerator. The precipitate which is deposited is filtered off with suction, washed with 30 ml of water and dried.

Yield: 290 mg (67% of theory) of 7-[(3aS,7aR)3a-amino-1,2,3,7a-tetrahydro-isoindol-2-yl]-8-chloro-1-[(1R,2S)-2-fluorocyclopropyl]-6-fluoro-1,4-dihydro-4-oxo-3-quinolinecarboxylic acid, melting point: 206°–207° C. (with decomposition), [α]$_D$: +2.5° (c=0.5, CHCl$_3$), variable results with respect to the optical resolution; structure confirmed by X-ray analysis.

217 mg (0.5 mmol) of 7-[(3aS,7aR)3a-amino-1,2,3,7a-tetrahydro-isoindol-2-yl]-8-chloro-1-[(1R,2S)-2-fluorocyclopropyl]-6-fluoro-1,4-dihydro-4-oxo-3-quinoline-carboxylic acid are dissolved in a mixture of 5 ml of water and 0.5 ml of 1n hydrochloric acid. The solution is lyophilised. 7-[(3aS,7aR)3a-amino-1,2,3,7a-tetrahydro-isoindol-2-yl]-8-chloro-1-[(1R,2S)-2-fluorocyclopropyl]-6-fluoro-1,4-dihydro-4-oxo-3-quinolinecarboxylic acid hydrochloride is isolated in quantitative yield.

Under similar conditions the corresponding mesylate and tosylate are prepared.

EXAMPLE 27

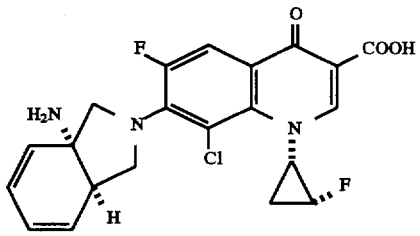

Under corresponding conditions to those in Example 26, using 8-chloro-6,7-difluoro-1-[(1S,2R)-2-fluorocyclopropyl]-1,4-dihydro-4-oxo-3-quinolinecarboxylic acid 7-([3aS ,7aR]3a-amino-1,2,3,7a-tetrahydro-isoindol-2-yl)-8-chloro-6-fluoro-1-[(1S,2R)-2-fluorocyclopropyl]-1,4-dihydro-4-oxo-3-quinolinecarboxylic acid of melting point: 170°–174° C. (with decomposition) is obtained in 71% yield, [α]$_D$:+215° (c=0.5, CHCl$_3$).

EXAMPLE 28

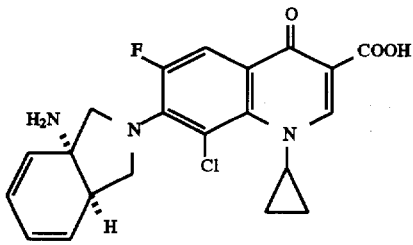

Under corresponding conditions to those in Example 26, using 8-chloro-1-cyclopropyl-6,7-difluoro-1,4-dihydro-4-oxo-3-quinolinecarboxylic acid 7-([3aS,7aR]3a-amino-1,2,3,7a-tetrahydro-isoindol-2-yl)-8-chloro-1-cyclopropyl-6-fluoro-1,4-dihydro-4-oxo-3-quinolinecarboxylie acid of melting point: 169°–170° C. (with decomposition) is obtained in 86% yield, $[\alpha]_D$: +116° (c=0.4, CHCl$_3$).

EXAMPLE 29

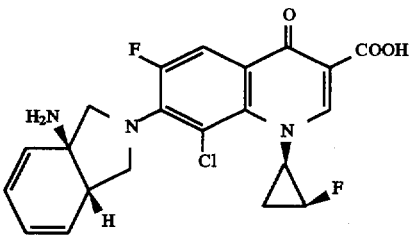

317 mg (1 mmol) of 8-chloro-6,7-difluoro-1-[(1R,2S)-2-fluorocyclopropyl]-1,4-dihydro-4-oxo-quinolinecarboxylic acid are heated under reflux for 1 hour with 187 mg (1.67 mmol) of 1,4-diazabicyclo[2.2.2]octane and 165 mg (1.2 mmol) of (3aR,7aS)-1,2,3,7a-tetrahydro-isoindol-3a-ylamine in a mixture of 4 ml of acetonitrile and 2 ml of dimethylformamide. The sohltion remains standing overnight in a refrigerator. The precipitate which is deposited is filtered off with suction, washed with 30 ml of water and dried.
Yield: 235 mg (54% of theory) of 7-([3aR,7aS]3a-amino-1,2,3,7a-tetrahydro-isoindol-2-yl)-8-chloro-1-[(1R,2S )-2-fluorocyclopropyl]-6-fluoro-1,4-dihydro-4-oxo-3-quinolinecarboxylic acid, melting point: 182°–183° C. (with decomposition), $[\alpha]_D$: –245° (c=0.5, CHCl$_3$).

EXAMPLE 30

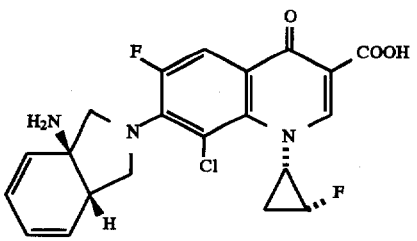

Under corresponding conditions to those in Example 29, using 8-chloro-6,7-difluoro-1-(1S,2R)-2-fluorocyclopropyl]-1,4-dihydro-4-oxo-3 -quinolinecarboxylic acid 7-([3aR,7aS]3a-amino-1,2,3,7a-tetrahydro-isoindol-2-yl)-8-chloro-6-fluoro-1-[(1S,2R)-2-fluorocyclopropyl]-1,4-dihydro-4-oxo-3-quinolineearboxylic acid of melting point: 195°–197° C. (with decomposition) is obtained in 71% yield, $[\alpha]_D$: –6.4° (c=0.5, CHCl$_3$), variable results with respect to the optical resolution.

EXAMPLE 31

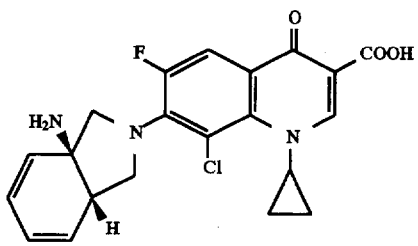

Under corresponding conditions to those in Example 29, using 8-chloro-6,7-difluoro-1-cyclopropyl-1,4-dihydro-4-oxo-3-quinolinecarboxylic acid 7-([3aR,7aS]3a-amino-1,2,3,7a-tetrahydro-isoindol-2-yl)-8-chloro-6-fluoro-1-cyclopropyl-1,4-dihydro-4-oxo-3-quinolinecarboxylic acid of melting point: 169°–170° C. (with decomposition) is obtained in 90% yield, $[\alpha]_D$: –119° (c=0.4, CHCl$_3$).

We claim:
1. Compounds of the formula (I)

$$T-Q \qquad (I)$$

in which
Q denotes a radical of the formula

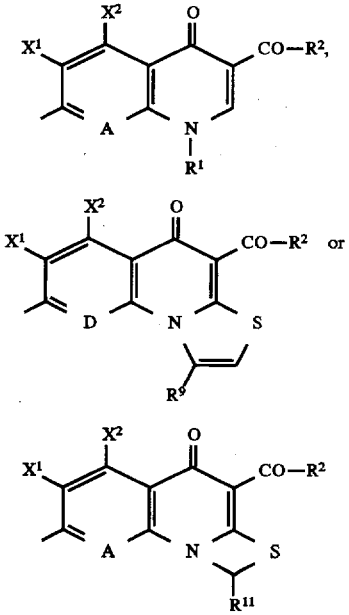

wherein
$R^1$ represents alkyl having 1 to 4 carbon atoms, which is optionally mono- or disubstituted by halogen or hydroxyl, alkenyl having 2 to 4 carbon atoms, cycloalkyl having 3 to 6 carbon atoms, which is optionally substituted by 1 or 2 fluorine atoms, bicyclo[1.1.1]pent-1-yl, 1,1-dimethylpropargyl, 3-oxetanyl, methoxy, amino, methylamino, dimethylamino, or phenyl which is optionally mono- or disubstituted by halogen, amino or hydroxyl,
$R^2$ represents hydroxyl, alkoxy having 1 to 3 carbon atoms, which is optionally substituted by hydroxyl, methoxy, amino or dimethylamino, benzyloxy or (5-methyl-2-oxo-1,3-dioxol-4-yl)-methyloxy, acetoxymethyloxy, pivaloyloxymethyloxy, 5-indanyloxy, phthalidinyloxy, 3-acetoxy-2-oxobutyloxy, nitromethyl or dialkoxycarbonylmethyl having 1 to 2 carbon atoms in each alkyl moiety, $R^9$ represents hydrogen or alicyl having 1 to 3 carbon atoms, which is optionally substituted by methoxy, hydroxy or halogen, $R^{11}$ represents hydrogen, $CH_3$ or $CH_2F$, $X^1$ represents halogen or nitro, $X^2$ represents hydrogen, halogen, amino, hydroxyl, methoxy, mercapto, methyl, halogenomethyl or vinyl, A represents N or C—$R^7$, wherein $R^7$ represents hydrogen, halogen, $CF_3$, $OCH_3$, $OCHF_2$, $CH_3$, CN, $CH=CH_2$ or $C\equiv CH$ or alternatively, together with $R^1$, can form a bridge of the structure

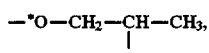

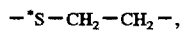

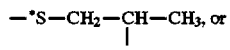

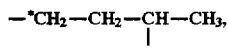

the atom marked by being linked to the carbon atom of A and

D represents N or C—$R^{10}$, wherein $R^{10}$ represents hydrogen, halogen, $CF_3$, $OCH_3$, $OCHF_2$ or $CH_3$ or alternatively, together with $R^9$, can form a bridge of the structure —*O—$CH_2$—, —*NH—$CH_2$—, —*N($CH_3$)—$CH_2$—, —*N($C_2H_5$)—$CH_2$—, —*N(c—$C_3H_5$)—$CH_2$— or —*S—$CH_2$—, the atom marked by * being linked to the carbon atom of D, and T denotes a radical of the formula

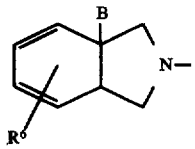

wherein

B represents $(CH_2)_m$—$NR^3R^4$ or $(CH_2)m$-$OR^5$, wherein m represents 0 or 1, $R^3$ represents hydrogen, methyl or alkoxycarboil having 1 to 4 carbon atoms in the alkyl moiety, $R^4$ represents hydrogen or methyl and $R^5$ represents hydrogen or methyl and $R^6$ represents hydrogen or methyl, and their pharmaceutically utilizable hydrates and acid addition salts and also the alkali metal, alkaline earth metal, silver and guanidinium salts of the underlying carboxylic acids.

2. Compounds of the formula (I) according to claim 1, in which

Q denotes a radical of the formula

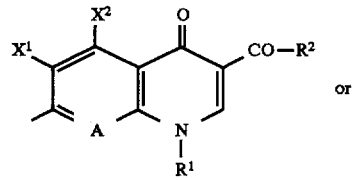 or

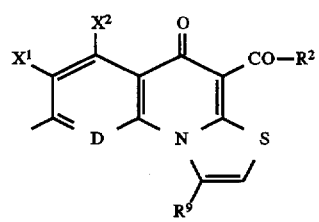

wherein $R^1$ represents alkyl having 1 to 4 carbon atoms, which is optionally mono- or disubstituted by halogen, alkenyl having 2 to 3 carbon atoms, cycloalkyl having 3 or 4 carbon atoms, which is optionally substituted by 1 fluorine atom, bicyclo [1.1.1]pent-1-yl 1,1-dimethylpropargyl, 3-oxetanyl, methylamino, or phenyl which is optionally mono- or disubstituted by fluorine, amino or hydroxyl, $R^2$ represents hydroxyl, alkoxy having 1 to 2 carbon atoms, benzyloxy or (5-methyl-2-oxo-1,3-dioxol-4-yl)-methoxy, $R^9$ represents hydrogen or alkyl having 1 to 2 carbon atoms, which is optionally mono- to trisubstituted by fluorine, $X^1$ represents fluorine or chlorine, $X^2$ represents hydrogen, halogen, amino, methyl, trifluoromethyl or vinyl, A represents N or C—$R^7$, wherein $R^7$ represents hydrogen, halogen, $CF_3$, $OCH_3$, $OCHF_2$, $CH_3$, CN, $CH=CH_2$ or $C\equiv CH$ or alternatively, together with $R^1$, can form a bridge of the structure

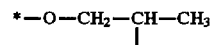

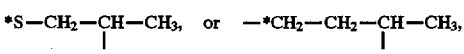

the atom marked by * being linked to the carbon atom of A and

D represents N or C—$R^{10}$, wherein $R^{10}$ represents hydrogen, fluorine, chlorine, $CF_3$, $OCH_3$ or $CH_3$ or alternatively, together with $R^9$, can form a bridge of the structure —*O—$CH_2$—, —*N($CH_3$)—$CH_2$—, —*N($C_2H_5$)—$CH_2$—, —*N(c—$C_3H_5$)—$CH_2$— or —*S—$CH_2$—, the atom marked by * being linked to the carbon atom of D, and T denotes a radical of the formula

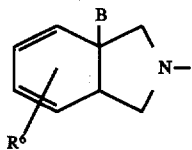

wherein
B represents —NR³R⁴ or —OH, wherein
R³ represents hydrogen or methyl,
R⁴ represents hydrogen or methyl and
R⁶ represents hydrogen and their pharmaceutically utilizable hyarates and acid addition salts and also the alkali metal, alkaline earth metal, silver and guanidinium salts of the underlying carboxylic acids.

3. Compounds of the formula (I) according to claim 1, in which
Q denotes a radical of the formula

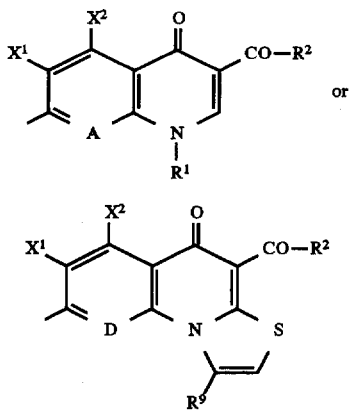

wherein
R¹ represents alkyl having 1 to 4 carbon atoms, which is optionally mono- or disubstituted by fluorine, vinyl, cyclopropyl which is optionally substituted by 1 fluorine atom, or phenyl which is optionally mono- or disubstituted by fluorine,
R² represents hydroxyl, alkoxy having 1 to 2 carbon atoms or (5-methyl-2-oxo-1,3-dioxol-4-yl)-methoxy,
R⁹ represents hydrogen or methyl which is optionally mono- to trisubstituted by fluorine,
X¹ represents fluorine,
X² represents hydrogen, fluorine, amino, methyl or vinyl,
A represents N or C—R⁷, wherein
R⁷ represents hydrogen, fluorine, chlorine, bromine, CF₃, OCH₃, OCHF₂, CH₃, CN, CH=CH₂ or C≡CH or alternatively, together with R¹, can form a bridge of the structure

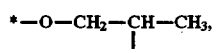

the atom marked by * being linked to the carbon atom of A and
D represents N or C—R¹⁰, wherein
R¹⁰ represents hydrogen, fluorine, chlorine or OCH₃ or alternatively, together with R⁹, can form a bridge of the structure —*O—CH₂—, —*N(CH₃)—CH₂—, —*N(C₂H₅)—CH₂- or —*S—CH₂—, the atom marked by * being linked to the carbon atom of D, and T denotes a radical of the formula

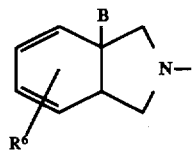

wherein
B represents NH₂ and
R⁶ represents hydrogen,
and their pharmaceutically utilizable hydrates and acid addition salts and also the alkali metal, alkaline earth metal, silver and guanidinium salts of the underlying carboxylic acids.

4. Diasteromerically pure and enantiomerically pure compounds according to claim 1.

5. A compound hydrate or salt thereof according to claim 1, wherein such compound is 7-(3a-amino-1,2,3,7a-tetrahydroisoindol-2-yl)-1-cyclopropyl-6,8-difluoro-1,4-dihydro-4-oxo-3-quinolinecarboxylic acid of the formula

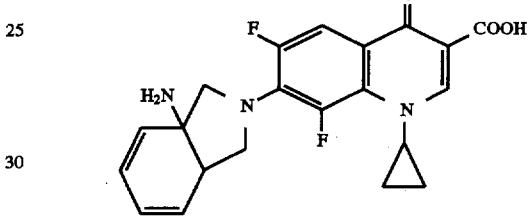

or a salt thereof.

6. A compound hydrate or salt thereof according to claim 1, wherein such compound is 7-(3a-amino-1,2,3,7a-tetrahydo-isoindol-2-yl)-8-chloro-1-cyclopropyl-6-fluoro-1,4-dihydro-4-oxo-3-quinolinecarboxylic acid of the formula

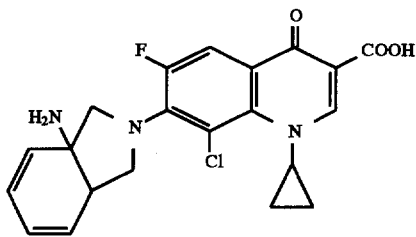

or a salt thereof.

7. A compound hydrate or salt thereof according to claim 1, wherein such compound is 7-(3a-amino-1,2,3,7a-tetrahydo-isoindol-2-yl)-1-cyclopropyl-6-fluoro-1,4-dihydro-8-methoxy-4-oxo-3-quinolinecarboxylic acid of the formula

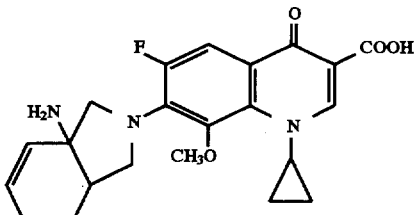

or a salt thereof.

8. A compound hydrate or salt thereof according to claim 1, wherein such compound is 7-(3a-amino-1,2,3,7a-tetrahydo-isoindol-2-yl)-6,8-difluoro-1-(cis-2-fluorocyclopropyl)-1,4-dihydro-4-oxo-3-quinolinecarboxylic acid of the formula.

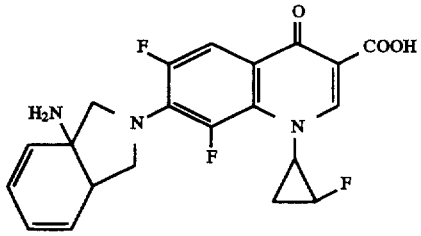

or a salt thereof.

9. A compound hydrate or salt thereof according to claim 1, wherein such compound is 7-(3a-amino-1,2,3,7a-tetrahydo-isoindol-2-yl)-1-cyclopropyl)-6-fluoro-1,4-dihydro-4-oxo-1,8-naphthyridine-3-carboxylic acid of the formula

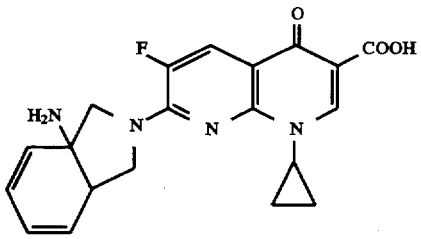

or a salt thereof.

10. An antibacterial composition comprising an antibacterially effective amount of a compound or salt thereof according to claim 1 and a diluent.

11. A method of combatting bacteria which comprises administering to a patient in need thereof an antibacterially effective amount of a compound or salt thereof according to claim 1.

12. The method according to claim 11 wherein such compound is 7-(3a-amino-1,2,3,7a-tetrahydroisoindol-2-yl)-1-cyclopropyl-6,8-difluoro-1,4-dihydro-4-oxo-3-quinolinecarboxylic acid of the formula

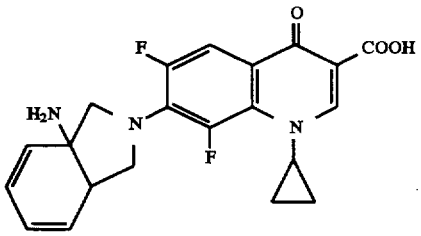

7-(3a-amino-1,2,3,7a-tetrahydo-isoindol-2-yl)-8-chloro-1-cyclopropyl-6-fluoro-1,4-dihydro-4-oxo-3-quinolinecarboxylic acid or the formula

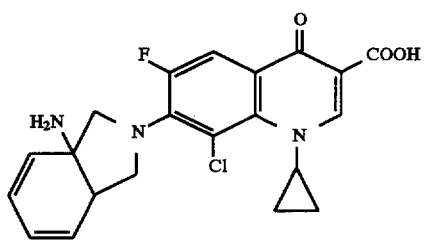

7-(3a-amino-1,2,3,7a-tetrahydo-isoindol-2-yl)-1-cyclopropyl-6-fluoro-1,4-dihydro-8-methoxy-4-oxo-3-quinolinecarboxylic acid or the formula

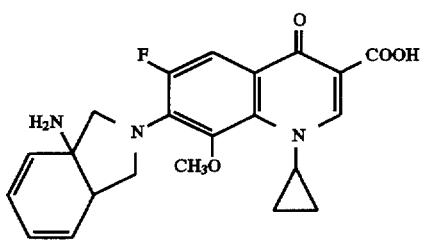

7-(3a-amino-1,2,3,7a-tetrahydo-isoindol-2-yl)-6,8-difluoro-1-(cis-2-fluorocyclopropyl)-1,4-dihydro-4-oxo-3-quinolinecarboxylic acid of the formula, or

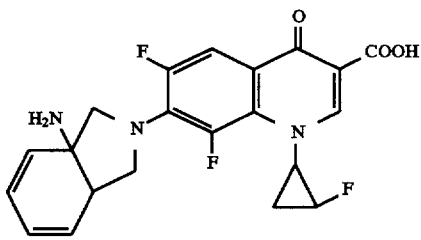

7-(3a-amino-1,2,3,7a-tetrahydo-isoindol-2-yl )-1-cyclopropyl)-6-fluoro-1,4-dihydro-4-oxo-1,8-naphthyridine-3-carboxylic acid of the formula

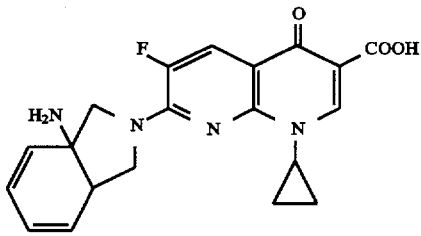

or a salt thereof.

13. Compounds of the formula (I)

T—Q  (I)

in which

Q denotes a radical of the formula

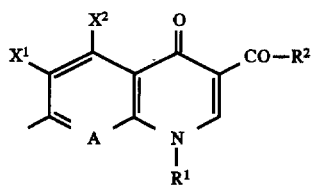

wherein
- $R^1$ represents alkyl having 1 to 4 carbon atoms, which is optionally mono- or disubstituted by halogen or hydroxyl, alkenyl having 2 to 4 carbon atoms, cycloalkyl having 3 to 6 carbon atoms, which is optionally substituted by 1 or 2 fluorine atoms, bicyclo[1.1.1]pent-1-yl, 1,1-dimethylpropargyl, 3-oxetanyl, methoxy, amino, methylamino, dimethylamino, or phenyl which is optionally toorio- or disubstituted by halogen, amino or hydroxyl,
- $R^2$ represents hydroxyl, alkoxy having 1 to 3 carbon atoms, which is optionally substituted by hydroxyl, methoxy, amino or dimethylamino, benzyloxy or (5-methyl-2-oxo-1,3-dioxol-4-yl)-methyloxy, acetoxymethyloxy, pivaloyloxymethyloxy, 5-indanyloxy, phthalidinyloxy, 3-acetoxy-2-oxo-butyloxy, nitromethyl or dialkoxycarbonylmethyl having 1: to 2 carbon atoms in each alkyl moiety,
- $X^1$ represents halogen or nitro,
- $X^2$ represents hydrogen, halogen, amino, hydroxyl, methoxy, mercapto, methyl, halogenomethyl or vinyl,
- A represents N or C—$R^7$, wherein
- $R^7$ represents hydrogen, halogen, $CF_3$, $OCH_3$, $OCHF_2$, $CH_3$, CN, $CH=CH_2$ or $C≡CH$,
- T denotes a radical of the formula

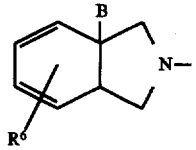

wherein
- B represents $(CH_2)_m$—$NR^3R^4$ or $(CH_2)_m$—$OR^5$, wherein m represents 0 or 1,
  - $R^3$ represents hydrogen, methyl or alkoxycarbonyl having 1 to 4 carbon atoms in the alkyl moiety,
  - $R^4$ represents hydrogen or methyl and
  - $R^5$ represents hydrogen or methyl and
- $R^6$ represents hydrogen or methyl, and their pharmaceutically utilizable hydrates and acid addition salts and also the alkali metal, alkaline earth metal, silver and guanidinium salts of the underlying carboxylic acids.

14. An antibacterial composition comprising an antibacterially effective amount of a compound or salt thereof according to claim 13 and a diluent.

15. A method of combatting bacteria which comprises administering to a patient in need thereof an antibacterially effective amount of a compound or salt thereof according to claim 13.

* * * * *

UNITED STATES PATENT AND TRADEMARK OFFICE
CERTIFICATE OF CORRECTION

PATENT : 5,679,689

DATED : October 21, 1997

INVENTOR(S) : Uwe Petersen, et al.

It is certified that error appears in the above-identified patent and that said Letters Patent is hereby corrected as shown below:

On the title page, under item [56] References Cited, insert under U. S. PATENT DOCUMENTS, the references shown below.

| | | | |
|---|---|---|---|
| 5,464,796 | 11/95 | Petersen et al. | 514/312 |
| 5,017,708 | 04/91 | Ogata et al. | 548/515 |
| 5,412,098 | 05/95 | Yasuhiro et al. | 546/156 |
| 5,166,203 | 11/92 | Kondo et al. | 514/230.5 |
| 5,126,337 | 06/92 | Ito et al. | 514/210 |
| 4,833,231 | 05/89 | Yoshida et al. | 528/423 |

UNITED STATES PATENT AND TRADEMARK OFFICE
CERTIFICATE OF CORRECTION

PATENT NO.   : 5,679,689
DATED        : October 21, 1997
INVENTOR(S)  : Uwe Petersen, et al.

It is certified that error appears in the above-identified patent and that said Letters Patent is hereby corrected as shown below:

| | |
|---|---|
| Col. 35, Line 33 | After "by" insert -- * -- |
| Col. 35, Line 56 | Delete "alkoxycarboil" and substitute --alkoxycarbonyl-- |
| Col. 38, Line 37 | Delete "tetrahydo--isoindol-2-yl)" and substitute --tetrahydro-isoindol-2-yl)-- |
| Col. 38, Line 53 | Delete tetrahydo--isoindol-2-yl)" and substitute --tetrahydro-isoindol-2-yl)-- |
| Col. 39, Line 3 | Delete "tetrahydo--isoindol-2-yl)" and substitute --tetrahydro-isoindol-2-yl)-- |
| Col. 39, Line 22 | Delete "tetrahydo--isoindol-2-yl)" and substitute --tetrahydro-isoindol-2-yl)-- |
| Col. 39, Line 65 | Delete "tetrahydo--isoindol-2-yl)" and substitute --tetrahydro-isoindol-2-yl)-- |
| Col. 40, Line 14 | Delete "tetrahydo--isoindol-2-yl)" and substitute --tetrahydro-isoindol-2-yl)-- |

UNITED STATES PATENT AND TRADEMARK OFFICE
CERTIFICATE OF CORRECTION

PATENT NO. : 5,679,689
DATED : October 21, 1997
INVENTOR(S) : Uwe Petersen, et al.

It is certified that error appears in the above-identified patent and that said Letters Patent is hereby corrected as shown below:

| | |
|---|---|
| Col 40, Line 30 | Delete "tetrahydo--isoindol-2-yl)" and substitute --tetrahydro-isoindol-2-yl)-- |
| Col 40, Line 46 | Delete "tetrahydo--isoindol-2-yl)" and substitute --tetrahydro-isoindol-2-yl)-- |
| Col. 41, Line 20 | Delete "toorio" and substitute --mono-- |

Signed and Sealed this

Eleventh Day of January, 2000

Attest:

Q. TODD DICKINSON

*Attesting Officer*     *Acting Commissioner of Patents and Trademarks*